(12) United States Patent
Drew et al.

(10) Patent No.: US 9,101,607 B2
(45) Date of Patent: Aug. 11, 2015

(54) METHOD FOR PRESERVING ALUM ADJUVANTS AND ALUM-ADJUVANTED VACCINES

(75) Inventors: Jeffrey Drew, London (GB); David Woodward, London (GB); Amanda Corteyn, London (GB)

(73) Assignee: Stabilitech Ltd., London (GB)

( * ) Notice: Subject to any disclaimer, the term of this patent is extended or adjusted under 35 U.S.C. 154(b) by 162 days.

(21) Appl. No.: 13/637,828

(22) PCT Filed: Mar. 31, 2011

(86) PCT No.: PCT/GB2011/000497
§ 371 (c)(1),
(2), (4) Date: Feb. 26, 2013

(87) PCT Pub. No.: WO2011/121305
PCT Pub. Date: Oct. 6, 2011

(65) Prior Publication Data
US 2013/0156797 A1 Jun. 20, 2013

(30) Foreign Application Priority Data
Mar. 31, 2010 (GB) .................................. 1005518.4
Mar. 31, 2010 (GB) .................................. 1005522.6

(51) Int. Cl.
| A61K 39/00 | (2006.01) |
| A61K 39/38 | (2006.01) |
| A61K 39/39 | (2006.01) |
| A61K 9/19 | (2006.01) |
| A61K 31/10 | (2006.01) |
| A61K 31/14 | (2006.01) |
| A61K 33/08 | (2006.01) |
| A61K 47/18 | (2006.01) |

(52) U.S. Cl.
CPC . *A61K 39/39* (2013.01); *A61K 9/19* (2013.01); *A61K 31/10* (2013.01); *A61K 31/14* (2013.01); *A61K 33/08* (2013.01); *A61K 47/183* (2013.01); *A61K 2039/55505* (2013.01)

(58) Field of Classification Search
CPC ....... A61K 31/10; A61K 31/14; A61K 33/08; A61K 47/183; A61K 9/19; A61K 39/00; A61K 9/1623
See application file for complete search history.

(56) References Cited

U.S. PATENT DOCUMENTS

| 3,927,208 A | 12/1975 | Zygraich et al. |
| 4,631,189 A | 12/1986 | Kendall et al. |
| 4,639,339 A | 1/1987 | Murashige et al. |
| 4,808,700 A | 2/1989 | Anderson et al. |
| 4,950,596 A | 8/1990 | Cheng et al. |
| 5,109,026 A | 4/1992 | Hoskinson et al. |
| 5,169,758 A | 12/1992 | Fischer et al. |
| 5,240,843 A | 8/1993 | Gibson et al. |
| 5,618,539 A | 4/1997 | Dorval et al. |
| 6,194,136 B1 | 2/2001 | Livesey et al. |
| 6,248,588 B1 | 6/2001 | Crespo et al. |
| 6,689,600 B1 | 2/2004 | Wu et al. |
| 7,235,391 B2 | 6/2007 | Wu et al. |
| 2004/0110267 A1 | 6/2004 | Sundar |
| 2004/0253574 A1 | 12/2004 | Schuler et al. |
| 2005/0239705 A1 | 10/2005 | Dake et al. |
| 2006/0073182 A1 | 4/2006 | Wong et al. |
| 2006/0154858 A1 | 7/2006 | Mattson et al. |
| 2006/0228334 A1 | 10/2006 | Rosa-Calatrava et al. |
| 2006/0247167 A1 | 11/2006 | Schlein et al. |
| 2008/0107631 A1 | 5/2008 | Wu et al. |
| 2009/0123436 A1 | 5/2009 | Opperman |
| 2013/0071431 A1 | 3/2013 | Drew et al. |
| 2013/0129685 A1 | 5/2013 | Drew et al. |

FOREIGN PATENT DOCUMENTS

| CN | 101670104 A | 3/2010 |
| EP | 0130619 A2 | 1/1985 |
| EP | 0156242 | 10/1985 |
| EP | 0376361 A2 | 7/1990 |
| EP | 0890362 A1 | 1/1999 |
| EP | 1946776 A1 | 7/2008 |
| EP | 1961761 A1 | 8/2008 |
| EP | 1133316 B1 | 1/2009 |
| JP | 60-193925 | 10/1985 |
| JP | 61189228 A | 8/1986 |
| JP | 2003095956 A | 4/2003 |
| JP | 2008513438 A | 5/2008 |
| JP | 2009510136 A | 3/2009 |
| JP | 2009526856 A | 7/2009 |
| WO | WO-90/05182 A1 | 5/1990 |
| WO | WO-94/04174 A1 | 3/1994 |

(Continued)

OTHER PUBLICATIONS

Tesconi et al., Journal of Pharmaceutical Sciences, May 1999, vol. 88, No. 5.*
Andersson et al., "Protein stabilising effect of polyethyleneimine" J Biotech. 72(1-2):21-31 (1999).
Andersson et al., "Stabilizing effect of chemical additives against oxidation of lactate dehydrogenase," Biotechnol Appl Biochem. 32:145-53 (2000).
Arakawa et al., "Factors affecting short-term and long-term stabilities of proteins ," Adv Drug Deliv Rev. 10:1-28 (1993).

(Continued)

*Primary Examiner* — Marcela M Cordero Garcia
*Assistant Examiner* — Kaipeen Yang
(74) *Attorney, Agent, or Firm* — Clark & Elbing LLP; Susan M. Michaud

(57) ABSTRACT

A method for preserving an aluminium-salt adjuvant during freezing or drying comprising freezing or drying an aqueous suspension or solution comprising: (a) an aluminium salt adjuvant; (b) a compound of formula (I) or a physiologically acceptable salt or ester thereof or a compound of formula (II) or a physiologically acceptable salt or ester thereof; and (c) optionally, one or more sugars.

19 Claims, 7 Drawing Sheets

(56) References Cited

FOREIGN PATENT DOCUMENTS

| WO | WO-95/11700 A1 | 5/1995 |
|---|---|---|
| WO | WO-97/04801 A1 | 2/1997 |
| WO | WO-97/15331 A1 | 5/1997 |
| WO | WO-99/27071 A1 | 6/1999 |
| WO | WO-00/29024 A1 | 5/2000 |
| WO | WO-01/29198 A1 | 4/2001 |
| WO | WO-01/93829 A2 | 12/2001 |
| WO | WO-02/101412 A2 | 12/2002 |
| WO | WO-03/035827 A2 | 5/2003 |
| WO | WO-2004/002534 A1 | 1/2004 |
| WO | WO-2004/035818 A1 | 4/2004 |
| WO | WO-2005/042029 A2 | 5/2005 |
| WO | WO 2005042029 A2 * | 5/2005 |
| WO | WO-2005/056808 A2 | 6/2005 |
| WO | WO-2005/062709 A2 | 7/2005 |
| WO | WO-2006/081587 A2 | 8/2006 |
| WO | WO-2006/085082 A1 | 8/2006 |
| WO | WO-2006/092668 A2 | 9/2006 |
| WO | WO-2006/094974 A2 | 9/2006 |
| WO | WO-2006/127150 A2 | 11/2006 |
| WO | WO-2007/038926 A1 | 4/2007 |
| WO | WO-2007/056847 A1 | 5/2007 |
| WO | WO-2007/095337 A2 | 8/2007 |
| WO | WO-2007/138135 A1 | 12/2007 |
| WO | WO-2008/051245 A2 | 5/2008 |
| WO | WO-2008/058035 A1 | 5/2008 |
| WO | WO-2008/114021 A1 | 9/2008 |
| WO | WO-2008/118691 A2 | 10/2008 |
| WO | WO-2008/150479 A2 | 12/2008 |
| WO | WO-2009/015343 A2 | 1/2009 |
| WO | WO-2010/035001 A1 | 4/2010 |

OTHER PUBLICATIONS

Arakawa et al., "Factors affecting short-term and long-term stabilities of proteins," Adv Drug Deliv Rev. 46(1-3):307-26 (2001).
Berge et al., "Preservation of enteroviruses by freeze-drying," Appl Microbiol. 22(5):850-3 (1971).
Braun et al., "Development of a freeze-stable formulation for vaccines containing aluminum salt adjuvants," Vaccine. 27(1):72-9 (2009).
Brown et al., "Assembly of hybrid bacteriophage Qbeta virus-like particles," Biochemistry. 48(47):11155-7 (2009).
Bryjak et al., "Storage stabilization and purification of enzyme by water-soluble synthetic polymers," Enzyme Microb Technol. 16:616-21 (1994).
Bryjak, "Storage stabilization of enzyme activity by poly(ethyleneimine)," Bioprocess Eng. 13:177-81 (1995).
Carpenter et al., "The mechanism of cryoprotection of proteins by solutes," Cryobiology. 25(3):244-55 (1988).
Chen et al., "Stabilization of recombinant human keratinocyte growth factor by osmolytes and salts," J Pharm Sci. 85(4):419-22 (1996).
Cleland et al., "Glycine betaine as a cryoprotectant for prokaryotes," J Microbiol Methods. 58(1):31-8 (2004).
"Composition of Medium 199," XP002596423 (2009). Retrieved from the Internet: <URL:http://www.fishersci.com/wps/downloads/segment/Scientific/pdf/cmbrex_medium_199.pdf.
Cosquer et al., "Nanomolar levels of dimethylsulfoniopropionate, dimethylsulfonioacetate, and glycine betaine are sufficient to confer osmoprotection to Escherichia coli," Appl Environ Microbiol. 65(8):3304-11 (1999).
Costantino et al., "Effect of excipients on the stability and structure of lyophilized recombinant human growth hormone," J Pharma Sci. 87(11):1412-20 (1998).
Drew et al., "Stable vaccine technology," displayed in Vienna Oct. 3 to 5, 2010.
Foreman et al., "Effects of charged water-soluble polymers on the stability and activity of yeast alcohol dehydrogenase and subtilisin Carlsberg," Biotechnol Bioeng. 76(3):241-6 (2001).
Greiff et al., "Effects of freezing, storage at low temperatures, and drying by sublimation in vacuo on the activities of measles virus," Nature. 202:624-5 (1964).
Gupta et al., "Stabilization of respiratory syncytial virus (RSV) against thermal inactivation and freeze-thaw cycles for development and control of RSV vaccines and immune globulin," Vaccine. 14(15):1417-20 (1996).
Holtmann et al., "Thermoprotection of Bacillus subtilis by exogenously provided glycine betaine and structurally related compatible solutes: involvement of Opu transporters," J Bacteriol. 186(6):1683-93 (2004).
Hubálek, "Protectants used in the cryopreservation of microorganisms," Cryobiology. 46(3):205-29 (2003).
Izutsu, "Stabilization of therapeutic proteins by chemical and physical methods" in Therapeutic Proteins, Smales and James ed. Humana Press ISBN 1-58829-390-4, 287-292 (2005).
Land et al., "The Challenges of Antimicrobial Preservation of a Sugar-free Liquid Risedronate Sodium Formulation for US and EMEA Pediatric Use," Post No. M1187. Procter & Gamble Pharmaceuticals, 2009 AAPS Natual Meeting and Exposition, Los Angeles, CA (2009).
Larski et al., "Stabilization of Newcastle disease virus by dimethyl sulfoxide," Acta Virol. 16(4):349-52 (1972).
Lever et al., "Using high-performance liquid chromatography to measure the effects of protein-stabilizing cosolvents on a model protein and fluorescent probes," Anal Biochem. 367(1):122-33 (2007).
Liao et al., "Influence of the active pharmaceutical ingredient concentration on the physical state of mannitol—implications in freeze-drying," Pharm Res. 22(11):1978-85 (2005). Abstract provided.
Liao et al., "Protective mechanism of stabilizing excipients against dehydration in the freeze-drying of proteins," Pharm Res. 19(12):1854-61(2002).
Manual of Policies and Procedures, Center for Drug Evaluation and Research, "Applications for Parenteral Products in Plastic Immediate Containers," MAPP 6020.2 (2007).
McGann et al., "Cryoprotection by dimethyl sulfoxide and dimethyl sulfone," Cryobiology. 24(1):11-6 (1987).
Nishigushi et al., "Temperature- and concentration-dependence of compatibility of the organic osmolyte beta-dimethylsulfoniopropionate," Cryobiology. 29(1):118-24 (1992).
Paleg et al., "Proline and glycine betaine influence protein solvation," Plant Physiol. 75(4):974-8 (1984).
Peek et al., "A rapid, three-step process for the preformulation of a recombinant ricin toxin A-chain vaccine," J Pharm Sci. 96(1):44-60 (2007).

Rathore et al. "Current perspectives on stability of protein drug products during formulation, fill and finish operations." Biotechnol Prog. 24(3):504-14 (2008).

Reichert et al., "Development trends for monoclonal antibody cancer therapeutics," Nat Rev Drug Discov. 6(5):349-56 (2007).

Sigalov, "Cryopreservation and long-term storage of human low density lipoproteins," Eur J Clin Chem Clin Biochem. 33(2):73-81 (1995).

Singh et al., "The osmoprotectants glycine and its methyl derivatives prevent the thermal inactivation of protective antigen of *Bacillus anthracis*," Biochem Biophys Res Comm. 316(2):559-64 (2004).

Sjölander et al., "ISCOMs: an adjuvant with multiple functions," J Leukoc Biol. 64(6):713-23 (1998).

Suntanto, et al. "Home delivery of heat stable vaccines in Indonesia: outreach immunization with a prefilled single use injection device" Bull. World. Health. Organ. 77(2):119-126 (1999).

Tiyaboonchai et al., "Insulin containing polyethylenimine-dextran sulfate nanoparticles," Int J Pharm. 255(1-2):139-51 (2003).

Wallis et al., "Stabilization of enveloped viruses by dimethyl sulfoxide," J Virol. 2(9):953-4 (1968).

Wolff et al., "Protection of aluminum hydroxide during lyophilisation as an adjuvant for freeze-dried vaccines," Colloids and Surfaces A: Physicochem. Eng Aspects. 330:116-26 (2008).

(56) References Cited

OTHER PUBLICATIONS

Wolff et al., "Comparative stability study of lyophilised aluminium hydroxide aduvanted vaccine formulations containing a monoclonal antibody as a model antigen and methods used for their characterisation," Colloids and Surfaces A: Physicochem. Eng Aspects. 339:82-93 (2009).

Wolff et al.,"Development of a formulation protecting aluminum hydroxide adjuvant vaccines during lyophilisation," 6th World Meeting on Pharmaceutics, Biopharmaceutics and Pharmaceutical Technology, Barcelona, Apr. 7 to 10, 2008.

Yancey, "Organic osmolytes as compatible, metabolic and counteracting cytoprotectants in high osmolarity and other stresses," J Exp Biol. 208:2819-30 (2005).

* cited by examiner

Normal adjuvant

Freeze damage

Figure 8
A a. Liquid
1             3
4             6
7             9
             12
10           15
13           18
16
B b. Frozen
1             3
4             6
7             9
10           12
13           15
16           18
Figure 9
A
1             3
4             6
7             9
             12
10           15
13           18
16
19           21
B
1             3
4             6
7             9
10           12
13       15
16           18
19           21
 Pipetting error

METHOD FOR PRESERVING ALUM ADJUVANTS AND ALUM-ADJUVANTED VACCINES

CROSS-REFERENCE TO RELATED APPLICATIONS

This application is the U.S. national stage filing under 35 U.S.C. §371 of international application PCT/GB2011/000497, filed Mar. 31, 2011, which claims priority from Great Britain Patent Application Nos. 1005522.6, filed Mar. 31, 2010, and 1005518.4, filed Mar. 31, 2010.

FIELD OF THE INVENTION

The invention relates to a method for preserving an aluminium salt adjuvant during freezing or drying, typically during freezing or drying of a vaccine preparation comprising an aluminium salt adjuvant and one or more vaccine antigens.

BACKGROUND TO THE INVENTION

Aluminium salt adjuvants are currently the most widely used adjuvants for human and veterinary vaccines. Aluminium adjuvant compounds include aluminium salts such as aluminium phosphate ($AlPO_4$) and aluminium hydroxide ($Al(OH)_3$) which are generically referred to in the field of vaccine adjuvants as "alum". To provide adequate immunogenicity, it is thought that antigens must be adsorbed onto the surface of the adjuvant. It is believed that alum adjuvants act as an immune system stimulus as well as providing a depot of antigen at the site of administration (e.g. by injection) thereby providing a gradual and continuous release of antigen to stimulate antibody production. Aluminium adjuvants in their natural form are commonly known as gels, which are particulate suspensions in aqueous media.

The storage and transportation of alum-adjuvanted vaccines is problematic. Freeze-drying (lyophilisation) is a process frequently used to improve long-term stability of various protein preparations. Nevertheless, commercial vaccine compositions containing aluminium salt adjuvants cannot be freeze-dried without causing damage to the adjuvant structure. Freeze-drying causes the collapse of the gel structure of the adjuvant resulting in aggregation and precipitation of the adjuvant salt on resuspension in water. The effect is to significantly reduce the immunogenicity of the vaccine.

WO 01/93829 describes a method of preparing an adjuvanted vaccine comprising spray-drying or spray freeze-drying an aqueous solution comprising:
(a) from 0.1 to 0.95% by weight of an aluminium salt or calcium salt adjuvant having an antigen adsorbed therein;
(b) from 0.5 to 6% by weight of a saccharide;
(c) from 0.1 to 2% by weight of an amino acid or salt thereof; and
(d) from 0.02 to 1% by weight of a colloidal substance.

WO 2008/118691 describes a method of preparing an immunologically-active adjuvant-bound dried vaccine composition comprising (a) combining at least one aluminium-salt adjuvant, at least one buffer system, at least one glass-forming agent and at least one antigen to create a liquid vaccine formulation; (b) freezing the liquid vaccine formulation to create a frozen vaccine formulation; and (c) lyophilizing the frozen vaccine formulation to create a dried vaccine composition. The glass-forming agent is preferably trehalose.

SUMMARY OF THE INVENTION

Surprisingly, the present inventors found that structural damage to an aluminium salt adjuvant can be reduced by freezing or drying, in particular freeze-drying, the adjuvant in the presence of a compound of formula (I) or (II) or a physiologically acceptable salt or ester thereof. The additional presence of one or more sugars can lead to a further reduction in the structural damage to the adjuvant during freezing or drying.

Accordingly, the present invention provides a method for preserving an aluminium-salt adjuvant during freezing or drying comprising freezing or drying an aqueous suspension or solution comprising:
(a) an aluminium salt adjuvant;
(b) a compound of formula (I) or a physiologically acceptable salt or ester thereof

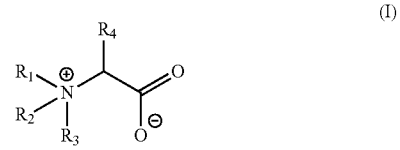

wherein:
$R_1$ represents hydrogen or $C_{1-6}$ alkyl; and
$R_4$ represents hydrogen; or
$R_1$ and $R_4$ together with the atoms to which they are attached form a pyrrolidine ring;
$R_2$ represents hydrogen, $C_{1-6}$ alkyl or $-(CH_2)_{2-5}NHC(O)(CH_2)_{5-15}CH_3$; and
$R_3$ represents $C_{1-6}$ alkyl; or
a compound of formula (II) or a physiologically acceptable salt or ester thereof

wherein:
X represents $-S(O)_2-$ or $-S^+(R_c)-$,
$R_a$ and $R_b$ independently represent $C_{1-6}$ alkyl; and
$R_c$ represents $C_{1-6}$ alkyl substituted with a carboxylate anion and with an amine ($-NH_2$) moiety; and
(c) optionally, one or more sugars.

The present invention also provides:
use of an excipient comprising (i) a compound of formula (I) or (II) of the invention or a physiologically acceptable salt or ester thereof and (ii) optionally, one or more sugars, for preserving an aluminium salt adjuvant during freezing or drying;
a vaccine composition comprising: an aluminium-salt adjuvant; one or more antigens; a compound of formula (I) or (II) of the invention or a physiologically acceptable salt or ester thereof; and optionally, one or more sugars.
a vaccine composition obtainable by the method of the invention; and
use of an excipient comprising (i) a compound of formula (I) or (II) of the invention or a physiologically acceptable salt or ester thereof and (ii) optionally one or more sugars, as a resuspension agent for a vaccine composition.

The frozen or dried vaccine compositions facilitate appropriate storage and maximize the shelf-life of the compositions. The compositions can be stock piled for prolonged periods of time. The immunogenicity, potency and efficacy of the vaccines can thus be maintained. The compound of formula (I) or (II) or physiologically acceptable salt or ester thereof and the optional sugar(s) act as cryoprotectants and protect the aluminium salt adjuvants against the stresses encountered during freezing and also as a lyoprotectant during freeze-drying.

BRIEF DESCRIPTION OF THE FIGURES

FIG. 8 shows the dot blot results from Example 7. FIG. 8A shows the dot blot of the samples set out in Table 19 stored at 4° C. FIG. 8B shows the dot blot of the samples set out in Table 19 stored at −80° C.

FIG. 9 shows more dot blot results from Example 7. FIG. 9A shows the dot blot of the samples set out in Table 20 stored at 4° C. FIG. 9B shows the dot blot of the samples set out in Table 20 stored at −80° C.

DETAILED DESCRIPTION OF THE INVENTION

Summary

Figure 1:
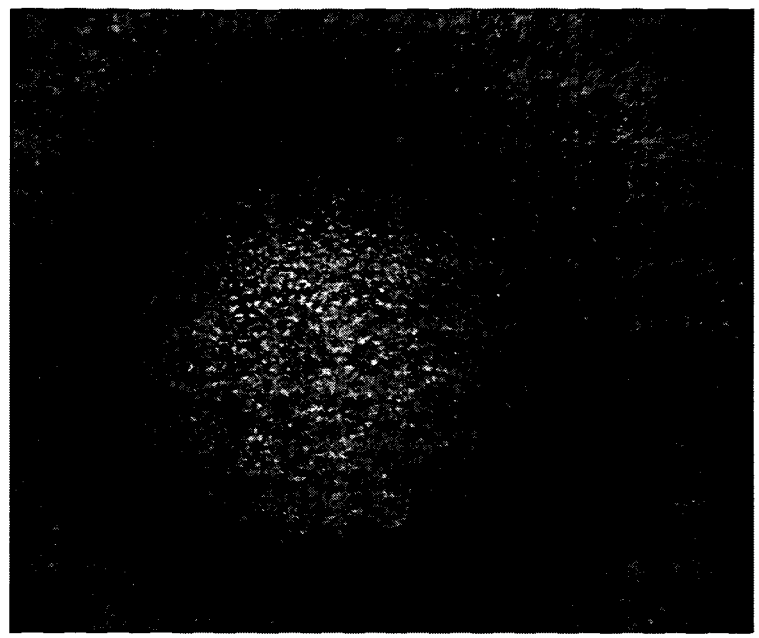
FIG. 1 shows the results of analysing adjuvants microscopically in the Reference Examples after freezing the aluminium hydroxide gel. Panel A shows an example of normal undamaged structure and panel B shows damaged agglomerated crystalline structure post-freezing of the aluminium hydroxide adjuvant.
Figure 1:
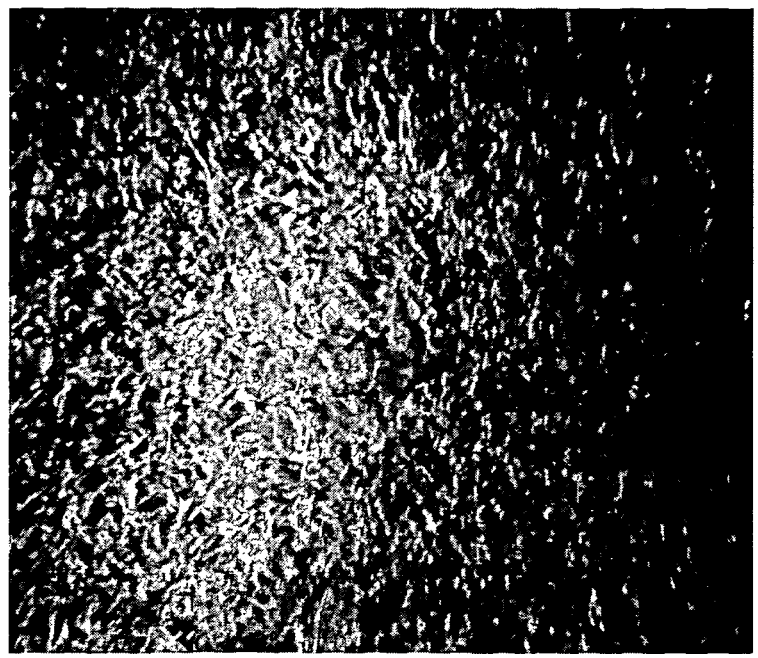

The present invention relates to the reduction and/or prevention of structural damage to aluminium salt vaccine adjuvants when frozen or dried, especially freeze-dried. Such structural damage is reduced or prevented by freezing or drying the adjuvant in the presence of a compound of formula (I) or (II) or physiologically acceptable salt or ester thereof and optionally (ii) one or more sugars.

The aluminium salt adjuvant, on which typically at least one antigen is adsorbed, is contacted with the compound of formula (I) or (II) or physiologically acceptable salt or ester thereof in aqueous solution. The resulting aqueous composition, in which one or more sugars may also be present, is then frozen or dried. When an antigen is present, the method is a method of preparing a vaccine composition comprising an aluminium salt adjuvant and at least one antigen. A vaccine preparation comprising the aluminium adjuvant can be thawed or reconstituted after freezing or drying respectively, prior to administration of the vaccine preparation to a patient.

The invention enables the structure and function of the aluminium adjuvant to be preserved during the freezing or drying step. The immunogenicity of aluminium adjuvanted vaccines following freezing or drying can consequently be maintained.

Aluminium Salt Adjuvant

Any type of aluminium salt suitable for use as an adjuvant may be used in the invention. The aluminium salt may be aluminium hydroxide (Al(OH)$_3$), aluminium phosphate (AlPO$_4$), aluminium hydrochloride, aluminium sulphate, ammonium alum, potassium alum or aluminium silicate. Preferably, the aluminium salt adjuvant used is aluminium hydroxide or aluminium phosphate. Most preferably, the aluminium salt adjuvant is aluminium hydroxide (Al(OH)$_3$).

Typically, the aluminium salt adjuvant takes the form of a hydrated gel made from an aluminium salt, the hydrated gel being a particulate suspension in aqueous media. The preparation of aluminium-salt adjuvants are well known to those skilled in the art. For example, aluminium hydroxide and aluminium phosphate adjuvants are generally prepared by exposing aqueous solutions of aluminium ions (typically as sulfates or chlorides) to alkaline conditions in a well-defined and controlled chemical environment, as known to those skilled in the art. Such methods can be used for example, to prepare an aluminium hydroxide or aluminium phosphate hydrated gel.

Antigen

An antigen suitable for use in the invention includes any immunogenic component of a vaccine. Thus, the antigen may be a protein, bacterial-specific protein, mucoprotein, glycoprotein, peptide, lipoprotein, polysaccharide, peptidoglycan, nucleoprotein or fusion protein.

The antigen may be derived from a microorganism (such as a bacterium, virus or fungus), a protozoan, a tumour, a malignant cell, a plant, an animal, a human, or an allergen. In one embodiment, the antigen is a protein but excludes a whole virus or virion.

The antigen may be synthetic, for example as derived using recombinant DNA techniques. The antigen may be a disease-related antigen such as a pathogen-related antigen, tumour-related antigen, allergy-related antigen, neural defect-related antigen, cardiovascular disease antigen, rheumatoid arthritis-related antigen. The antigen may be an inactivated or attenuated/detoxifed toxin (toxoid).

In particular, the pathogens from which the vaccine immunogen is derived may include human papilloma viruses (HPV), HIV, HSV2/HSV1, influenza virus (types A, B and C), para influenza virus, polio virus, RSV virus, rhinoviruses, rotaviruses, hepaptitis A virus, norwalk virus, enteroviruses, astroviruses, measles virus, mumps virus, varicella-zoster virus, cytomegalovirus, epstein-barr virus, adenoviruses, rubella virus, human T-cell lymphoma type I virus (HTLV-I), hepatitis B virus (HBV), hepatitis C virus (HCV), hepatitis D virus, poxvirus, vaccinia virus, *Salmonella, Neisseria, Borrelia, Chlamydia, Clostridium* such as *C. difficile* and *C. tetani, Bordetella* such as *Bordetella pertussis, Corynebacterium* such as *C. diptheriae, Plasmodium, Coxoplasma, Pneumococcus, Meningococcus, Cryptococcus, Streptococcus, Vibriocholerae, Staphylococcus, Haemophilus, Bacillus* such as *Bacillus anthracis* (anthrax), *Escherichia, Candida, Aspergillus, Entamoeba, Giardia* and *Trypanasoma*.

The vaccine may further be used to stimulate a suitable immune response against numerous veterinary diseases. The vaccine antigen may therefore be derived from a foot and mouth disease virus (including serotypes O, A, C, SAT-1, SAT-2, SAT-3 and Asia-1), coronavirus, bluetongue virus, feline leukaemia virus, avian influenza virus, hendra and nipah virus, pestivirus such as bovine viral diarrhoea virus and canine parvovirus.

Tumor-associated antigens include for example, melanoma-associated antigens, mammary cancer-associated antigens, colorectal cancer-associated antigens or prostate cancer-associated antigens An allergen-related antigen includes any allergen antigen suitable for use in a vaccine to stimulate suppression of an allergic reaction in an individual to which the vaccine is administered (e.g. antigens derived from pollens, dust mites, insects, food allergens, dust, poisons, toxins, venoms and parasites).

Compound of Formula (I) or (II) or Physiologically Acceptable Salt or Ester Thereof The compound of formula (I) and (II) may be present as a physiologically acceptable salt or ester thereof.

The salt is typically a salt with a physiologically acceptable acid and thus includes those formed with an inorganic acid such as hydrochloric or sulphuric acid or an organic acid such as citric, tartaric, malic, maleic, mandelic, fumaric or methanesulphonic acid. The hydrochloride salt is preferred.

The ester is typically a $C_{1-6}$ alkyl ester, preferably a $C_{1-4}$ alkyl ester. The ester may therefore be the methyl, ethyl, propyl, isopropyl, butyl, isobutyl or tert-butyl ester. The ethyl ester is preferred.

As used herein, a $C_{1-6}$ alkyl group is preferably a $C_{1-4}$ alkyl group. Preferred alkyl groups are selected from methyl, ethyl, propyl, isopropyl, butyl, isobutyl and tert-butyl. Methyl and ethyl are particularly preferred.

For the avoidance of doubt, the definitions of compounds of formula (I) and formula (II) also include compounds in which the carboxylate anion is protonated to give —COOH and the ammonium or sulfonium cation is associated with a pharmaceutically acceptable anion. Further, for the avoidance of doubt, the compounds defined above may be used in any tautomeric or enantiomeric form.

Compounds of Formula (I)

Typically, $R_1$ represents hydrogen or $C_{1-6}$ alkyl and $R_4$ represents hydrogen. Typically, $R_2$ represents hydrogen or $C_{1-6}$ alkyl. Preferably, $R_1$ represents hydrogen or $C_{1-6}$ alkyl, $R_4$ represents hydrogen and $R_2$ represents hydrogen or $C_{1-6}$ alkyl.

Preferably, the compound of formula (I) is an N—$C_{1-6}$ alkyl-, N,N-di($C_{1-6}$ alkyl)- or N,N,N-tri($C_{1-6}$ alkyl)-glycine or physiologically acceptable salt or ester thereof. The alkyl group is typically a $C_{1-4}$ alkyl group. Preferred alkyl groups are selected from methyl, ethyl, propyl, isopropyl, butyl, isobutyl and tert-butyl. Methyl and ethyl are particularly preferred.

Preferred compound of formula (I) are N-methylglycine, N,N-dimethylglycine or N,N,N-trimethylglycine or physiologically acceptable salts or esters thereof. N-Methyl-glycine is also called sarcosine. N,N-Dimethylglycine is also termed dimethylglycine (DMG) or 2-(dimethylamino)-acetic acid. N,N,N-trimethylglycine is termed trimethylglycine (TMG).

Alternatively, the compound of formula (I) is typically a glycine derivative of formula (IA) or a physiologically acceptable salt or ester thereof:

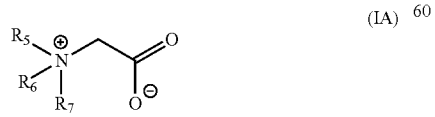

(IA)

wherein $R_5$ and $R_6$ independently represent $C_{1-6}$ alkyl, for example $C_{1-4}$ alkyl such as methyl or ethyl; and $R_7$ represents $C_{1-6}$ alkyl, for example $C_{1-4}$ alkyl such as methyl or ethyl, or —$(CH_2)_{2-5}NHC(O)(CH_2)_{5-15}CH_3$. Preferred compounds of formula (IA) are trimethylglycine (TMG) and cocamidopropyl betaine (CAPB) or physiologically acceptable salts or esters thereof.

Alternatively, the compound of formula (I) is typically a proline derivative of formula (IB) or a physiologically acceptable salt or ester thereof:

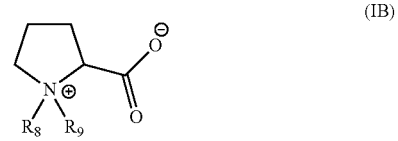

(IB)

wherein $R_8$ and $R_9$ independently represent $C_{1-6}$ alkyl, for example $C_{1-4}$ alkyl such as methyl or ethyl. Preferably the compound of formula (IB) is an S-proline derivative. Preferably $R_8$ and $R_9$ both represent methyl; this compound is known as proline betaine. S-proline betaine or physiologically acceptable salt or ester thereof is particularly preferred:

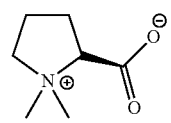

Compounds of formula (IA) or physiologically acceptable salts or esters thereof are preferred.

Most preferably, the compound of formula (I) is N,N-dimethylglycine or physiologically acceptable salt or ester thereof.

Compounds of Formula (II)

Typically, the carboxylate and amine substituents of $R_c$ are attached to the same carbon atom of the $R_c$ alkyl moiety. Typically $R_c$ is a $C_{2-4}$ or $C_{2-3}$ alkyl moiety.

The compound of formula (II) is typically a sulfone compound of formula (IIA) or a physiologically acceptable salt or ester thereof:

(IIA)

wherein $R_c$ and $R_d$ independently represent $C_{1-6}$ alkyl, for example $C_{1-4}$ alkyl such as methyl or ethyl. A preferred sulfone compound is methylsulfonylmethane (MSM), which is also known as dimethylsulfone ($DMSO_2$).

The compound of formula (II) is typically a compound of formula (IIB) or a physiologically acceptable salt or ester thereof:

(IIB)

wherein $R_e$ and $R_f$ independently represent $C_{1-6}$ alkyl, for example $C_{1-4}$ alkyl such as methyl or ethyl, and $R_g$ represents $C_{1-6}$ alkyl, for example $C_{1-4}$ alkyl such as methyl or ethyl, substituted with a carboxylate anion and with an amine ($-NH_2$) moiety. A preferred compound of formula (IIB) is S-methyl-L-methionine (SMM) or a physiologically acceptable salt or ester thereof.

Sugars

Sugars suitable for use in the present invention include reducing sugars such as glucose, fructose, glyceraldehydes, lactose, arabinose and maltose; and preferably non-reducing sugars such as sucrose and raffinose. The sugar may be a monosaccharide, disaccharide, trisaccharide, or other oligosaccharides. The term "sugar" includes sugar alcohols.

Monosaccharides such as galactose and mannose; dissaccharides such as sucrose, lactose and maltose; trisaccharides such as raffinose and tetrasaccharides such as stachyose are envisaged. Trehalose, umbelliferose, verbascose, isomaltose, cellobiose, maltulose, turanose, melezitose and melibiose are also suitable for use in the present invention. A suitable sugar alcohol is mannitol.

Two or more sugars may be present. Two, three or four sugars may be used. When one or more sugars are present in the aqueous suspension that is frozen or freeze-dried, preferably sucrose or sucrose and raffinose are present. Sucrose is a disaccharide of glucose and fructose. Raffinose is a trisaccharide composed of galactose, fructose and glucose.

Aqueous Suspension to be Frozen or Dried

The aqueous suspension or solution to be frozen or dried can be prepared by admixing the aluminium salt adjuvant with an aqueous solution of the compound of formula (I) or (II) or physiologically acceptable salt or ester thereof. The compound of formula (I) or (II) or physiologically acceptable salt or ester thereof may in particular be selected from dimethylglycine, S-methyl-L-methionine, methylsulfonylmethane, sarcosine and trimethylglycine, and may for example be dimethylglycine, S-methyl-L-methionine, methylsulfonylmethane or trimethylglycine. Any suitable aqueous solution may be used. The solution may be buffered. The solution may be a HEPES, Tris-buffered, phosphate-buffered or pure water solution.

Optionally one or more sugars is dissolved in the aqueous solution prior to admixture with the adjuvant. Alternatively the sugar(s) can be admixed with the suspension of the adjuvant in the aqueous solution of the compound of formula (I) or (II) or physiologically acceptable salt or ester thereof.

Where present, the antigen(s) are generally adsorbed onto the adjuvant prior to admixture of the adjuvant with the aqueous solution of the compound of formula (I) or (II) or physiologically acceptable salt or ester thereof. The adjuvants can be prepared in the form of a hydrated gel and the antigen adsorbed into the hydrated gel. Antigen adsorption can be carried out using techniques well known to those skilled in the art. For example, for certain protein antigens, adsorption may best be carried out at a pH interval where the adjuvant and antigen will have opposite electrical charges, facilitating electrostatic attraction and adsorption. Protein adsorption for a particular antigen-adjuvant combination will depend on the nature of the antigen and the chemical environment (pH, ionic strength, presence of surfactants etc).

The concentrations of the compound of formula (I) or (II) or physiologically acceptable salt or ester thereof and of the or each sugar in the aqueous suspension or solution to be frozen or can be determined by routine experimentation. Optimised concentrations can thus be selected. The compound of formula (I) or (II) or physiologically acceptable salt or ester thereof can act synergistically with the sugar(s) to improve stability.

The concentration of the compound of formula (I) or (II) or physiologically acceptable salt or ester thereof in the aqueous suspension or solution is typically in the range of 0.001M or more, preferably in the range of 0.01M or more and more preferably 0.1M or more, for example from 0.1M to 5.0M. The particular concentration that is employed will depend on several factors including, where present, the nature of the antigen; the particular compound of formula (I) or (II) or physiologically acceptable salt or ester thereof being used; whether one or more sugar is being used and if so the identity of the sugar(s); and the particular freezing or drying procedure that is adopted. Thus:

The concentration of a compound of formula (I) or a compound of formula (IA) or formula (IB), such as TMG, or a physiologically acceptable salt or ester thereof is preferably from 0.01M to 5M, from 0.1M to 5M, from 0.2M to 5.0M or from 0.1M to 1M.

The concentration of a compound of formula (II) in which X represents $-S(O)_2-$ or a compound of formula (IIA), such as MSM, or a physiologically acceptable salt or ester thereof is preferably from 0.01M to 4M, from 0.05M to 2M or from 0.07M to 1M or even to 0.53M.

The concentration of a compound of formula (II) in which X represents $-S^+(R_c)-$ or a compound of formula (IIB), such as S-methyl-L-methionine, or a physiologically acceptable salt or ester thereof is preferably from 0.01M to 5M, from 0.1M to 5M, from 0.2M to 3M or from 0.1M to 1M.

The concentration of a compound of formula (I) which is a N,N-di($C_{1-6}$ alkyl)-, N,N,N-tri($C_{1-6}$alkyl)-, or N—$C_{1-6}$ alkyl-glycine, such as N,N-dimethylglycine, N,N,N-trimethylglycine, or N-methylglycine, or a physiologically acceptable salt or ester thereof is typically 0.01M or more and preferably 0.1M or more, for example from 0.1M to 5.0M, from 0.33M to 5.0M, from 0.5M to 4M or from 0.5M to 3M.

The concentration of a compound of formula (I) which N,N-dimethylglycine (DMG) or a physiologically acceptable salt or ester thereof is typically 0.01M or more and preferably 0.1M or more, for example from 0.1M to 5.0M, from 0.33M to 5.0M, from 0.5M to 4M or from 0.5M to 3M. Less DMG or DMG salt or ester can be employed when one or more sugars are present.

If one or more sugar(s) is used, the concentration of sugar or total concentration of sugar in the aqueous suspension or solution that is to be frozen or dried is typically 1M or less or 0.7M or less, for example 0.5M or less or 0.29M or less. A 10% w/v sucrose solution has a sucrose concentration of 0.29M. The sugar concentration or the total concentration may be down to 0.1 mM, to 0.5 mM, to 0.073M or to 0.146M.

When the compound of formula (I) or (II) or physiologically acceptable salt or ester thereof is DMG or a physiologically acceptable salt or ester thereof, the concentration of sugar, if present, in the aqueous suspension or solution for freezing or drying is typically 1M or less or 0.7M or less, for example 0.5M or less or 0.29M or less. A 10% w/v sucrose solution has a sucrose concentration of 0.29M. Preferably, the concentration of the sugar such as sucrose or raffinose or, if more than one sugar is present, the total concentration of sugar is 0.5M or less, 0.2M or less, 0.1M or less or 10 mM or less. The minimum concentration of the sugar if present or, if more than one sugar is present, the minimum total concentration of sugar may be 0.01M, 0.1M or 0.2M. The sugar concentration, for example the concentration of sucrose or raffinose, or the total concentration if more than one sugar is present may thus be from 0.01M to 0.7M, from 0.029M to 0.5M, from 0.058M to 0.3M or from 0.1M to 0.3M. When the sugar is sucrose, the concentration of sucrose is preferably from 0.01 to 0.2M and the concentration of DMG or salt or ester thereof is preferably from 0.2 to 2M.

The particular concentration that is employed will depend on several factors including the nature of the antigen, the particular the compound of formula (I) or (II) or physiologically acceptable salt or ester thereof being used and the particular freezing or drying procedure that is adopted. The sugar concentration or the total concentration may be from 0.1 mM to 0.7M, from 5 mM to 0.7M, from 0.073M to 0.5M, or from 0.146M to 0.389M.

When the sugar is mannitol, the mannitol concentration is typically 0.2 to 1M or 0.2 to 0.8M, preferably 0.25 to 0.6M or 0.4 to 0.8M, for example 0.5 to 0.6M.

The most effective concentration of the compound of formula (I) or (II) or physiologically acceptable salt or ester thereof will depend on the particular type of compound used, whether it is used in combination with a sugar and the type of aluminium salt adjuvant that is used e.g. whether an aluminium hydroxide or aluminium phosphate adjuvant is used. Using a mixture of a compound of formula (I) or (II) or physiologically acceptable salt or ester thereof together with a sugar, the inventors have demonstrated that lower concentrations of each component can be used to achieve the same level of protection of the adjuvant as that obtained when each component is used separately.

Highly concentrated solutions of sugars have been known to give site-specific reactions when vaccine preparations containing such concentrated sugars are injected into patients. Therefore, the invention has the advantage that lower concentrations of sugars can be used when in combination with a compound of formula (I) or (II) or physiologically acceptable salt or ester thereof. As a result, when such vaccine preparations are reconstituted or thawed, the concentration of sugar is reduced and the likelihood of site-specific reaction is minimised.

Freezing/Drying
Freezing

Freezing is conducted by any suitable method. Freezing may thus be carried out by immersing in liquid nitrogen or liquid nitrogen vapour, placing in a freezer at a temperature of from −4° C. to −80° C. or using a dry ice and alcohol freezing bath. At atmospheric pressure, temperatures such as −4° C. or below, −10° C. or below, −15° C. or below, −20° C. or below, −25° C. or below may be used.

Drying

Typically, drying is achieved by freeze-drying, vacuum drying, spray-drying, spray freeze-drying or fluid bed drying. Freeze-drying is preferred. By reducing the water in the material and sealing the material in a vial, the material can be easily stored, shipped and later reconstituted to its original form. The drying conditions can be suitably optimised via routine experimentation.

On drying, a composition is formed which incorporates the viral particles. A matrix incorporating the viral particles is thus produced. The composition is typically an amorphous solid. A solid matrix, generally an amorphous solid matrix, is thus generally formed. By "amorphous" is meant non-structured and having no observable regular or repeated organization of molecules (i.e. non-crystalline). The drying procedure can be effected to form an amorphous cake e.g. by freeze-drying.

Freeze-Drying

Freeze-drying can be carried out according to standard procedures. There are three main stages: freezing, primary drying and secondary drying. Freezing is typically performed using a freeze-drying machine. In this step, it is important to cool the biological material below its eutectic point, the lowest temperature at which the solid and liquid phase of the material can coexist. This ensures that sublimation rather than melting will occur in the following steps. Alternatively, amorphous materials do not have a eutectic point, but do have a critical point, below which the product must be maintained to prevent melt-back or collapse during primary and secondary drying.

During primary drying the pressure is controlled by the application of appropriate levels of vacuum whilst enough heat is supplied to enable the water to sublimate. At least 50%, typically 60 to 70%, of the water in the material is sublimated at this stage. Primary drying may be slow as too much heat could degrade or alter the structure of the biological material. A cold condenser chamber and/or condenser plates provide surfaces on which the water vapour is trapped by resolidification.

In the secondary drying process, water of hydration is removed by the further application of heat. Typically, the pressure is also lowered to encourage further drying. After completion of the freeze-drying process, the vacuum can either be broken with an inert gas such as nitrogen prior to sealing or the material can be sealed under vacuum.

Vacuum Drying

In certain embodiments, drying is carried out using vacuum desiccation at around 1300 Pa. However vacuum desiccation is not essential to the invention and in other embodiments, the preservation mixture contacted with the viral particle is spun (i.e. rotary desiccation) or freeze-dried (as further described below). Advantageously, the method of the invention further comprises subjecting the preservation mixture containing the viral particle to a vacuum. Conveniently, the vacuum is applied at a pressure of 20,000 Pa or less, preferably 10,000 Pa or less. Advantageously, the vacuum is applied for a period of at least 10 hours, preferably 16 hours or more. As known to those skilled in the art, the period of vacuum application will depend on the size of the sample, the machinery used and other parameters.

Spray-Drying and Spray Freeze-Drying

In another embodiment, drying is achieved by spray-drying or spray freeze-drying the viral particles admixed with the preservation mixture of the invention. These techniques are well known to those skilled in the art and involve a method of drying a liquid feed through a gas e.g. air, oxygen-free gas or nitrogen or, in the case of spray freeze-drying, liquid nitrogen. The liquid feed is atomized into a spray of droplets. The droplets are then dried by contact with the gas in a drying chamber or with the liquid nitrogen.

Fluid Bed Drying

In a further embodiment, drying is achieved by fluid bed drying the viral particles admixed with the preservation mixture of the invention. This technique is well known to those skilled in the art and typically involves passing a gas (e.g. air) through a product layer under controlled velocity conditions to create a fluidized state. The technique can involve the stages of drying, cooling, agglomeration, granulation and coating of particulate product materials.

Heat may be supplied by the fluidization gas and/or by other heating surfaces (e.g. panels or tubes) immersed in the fluidized layer. Cooling can be achieved using a cold gas and/or cooling surfaces immersed in the fluidized layer. The steps of agglomeration and granulation are well known to those skilled in the art and can be performed in various ways depending on the product properties to be achieved. Coating of particulate products such as powders, granules or tablets can be achieved by spraying a liquid on the fluidized particles under controlled conditions.

The composition that is produced by the freezing or drying is typically a solid matrix having a low residual moisture content. A level of residual moisture content is achieved which offers long term preservation of vaccine activity at temperatures greater than refrigeration temperatures, e.g. from 4° C. to 56° C. or more, or lower than refrigeration temperatures, e.g. from 0° C. to −70° C. or below. The composition that is produced according to the invention may thus have a residual moisture content of 5% or less, 2% or less or 1% or less by weight. Typically the composition has residual moisture content of from 0.1 to 5% or from 0.5 to 5%.

The composition can be obtained in dry powder form. A cake resulting from the drying, e.g. freeze-drying step can be milled to powder form. A solid composition according to the invention thus may take the form of free-flowing particles. The solid composition is typically provided as a powder in a sealed vial, ampoule or syringe. If for inhalation the powder can be provided in a dry powder inhaler. The solid matrix can alternatively be provided as a patch. A powder may be compressed into tablet form.

The composition may consist, or consist essentially, of: the aluminium-salt adjuvant; one or more antigens; the compound of formula (I) or (II) or a physiologically acceptable salt or ester thereof; and optionally one or more sugars.

Use of Compositions of the Invention

The frozen or dried vaccine compositions are converted into liquid form (aqueous solution) prior to administration to a patient. A frozen composition is thawed and diluted as necessary with e.g. phosphate-buffered saline or Water for Injections. A dried composition is reconstituted as an aqueous solution, for example by phosphate-buffered saline or Water for Injections. The resulting aqueous solution can then be administered, e.g. by injection, to a patient in need of vaccination.

The compound of formula (I) or (II) or a physiologically acceptable salt or ester thereof and, optionally, one or more sugars, typically acts as a resuspension agent for the vaccine composition, for example when it is converted into liquid form (aqueous solution) prior to administration to a patient.

Protection Against Adverse Effects of Freezing or Drying

Aluminium salt adjuvants in their natural form are commonly in the form of gels that are particulate suspensions in aqueous media. Freezing or drying often causes structural alterations typified by an increased particle size with corresponding increased sedimentation rates and tighter packing of the sedimented solid compounds. Using the present invention, however, damage in the form of increased particle size, increased sedimentation rate and/or tighter packing of sedimented solids as a result of freezing or freeze-drying can be reduced.

Structural damage in the form of increased particle size with corresponding increased sedimentation rates and tighter packing of the sedimented solid compounds can been assessed using the adjuvant agglomeration assay described in Example 1. Other analytical methods for assessing the physiochemical characteristics of aluminium adjuvants before and after freezing or freeze-drying may also be used. For example, particle size distributions of the aluminium gel particles can be obtained using laser diffraction analysis, X-ray diffraction or infrared spectroscopy. Microscopy can also be used to visualise structural changes.

The following Examples illustrate the invention. A Reference Example is also provided.

REFERENCE EXAMPLE

Adjuvant

Aluminium hydroxide gel $(Al(OH)_3)$ was obtained from Sigma (A8222) as a 13 mg/ml solution (with a pH of 6.8).

Freezing the Adjuvant

The adjuvant was frozen by being placed in a laboratory freezer where it was left overnight at −20° C. It was then allowed to thaw at and equilibrate to room temperature (approximately 20° C.).

Microscopic Analysis

Adjuvants were examined microscopically at a magnification of 100×. Examples of the normal, undamaged amorphous structure and damaged agglomerated crystalline structure post-freezing of aluminium hydroxide are shown in FIG. 1. Photograph A shows the evenly distributed particulate suspension of undamaged adjuvant compared with photograph B which shows the formation of large agglomerated flat crystal structures typical of freeze-damaged adjuvant.

Example 1

Methods

The aluminium hydroxide adjuvant was obtained from Sigma (A8222) as a 13 mg/ml solution at pH 6.8. Initially, 50 µl volumes of the aluminium hydroxide were added to 100 µl volumes of sucrose and/or a further excipient diluted in Dulbecco's phosphate buffered saline (PBS) in wells of 96 well flat bottomed microplates. The further excipient was DMG. A list of final concentrations of DMG and sucrose before freezing can be seen in Table 1 below.

The adjuvants were frozen at −20° C. After approximately 18 hours samples containing $Al(OH)_3$ were thawed and assessed for sediment levels as described using the adjuvant agglomeration assay described below.

TABLE 1

| Excipient | Excipient Concentration (M) | Sucrose Concentration (mM) |
|---|---|---|
| DMG | 1 | 234 |
| DMG | 0.33 | 234 |
| DMG | 0.1 | 234 |
| DMG | 0 | 234 |
| DMG | 1 | 117 |
| DMG | 0.33 | 117 |
| DMG | 0.1 | 117 |
| DMG | 0 | 117 |
| DMG | 1 | 58 |
| DMG | 0.33 | 58 |
| DMG | 0.1 | 58 |
| DMG | 0 | 58 |
| DMG | 1 | 29 |
| DMG | 0.33 | 29 |
| DMG | 0.1 | 29 |
| DMG | 0 | 29 |
| DMG | 1 | 0 |
| DMG | 0.33 | 0 |
| DMG | 0.1 | 0 |
| DMG | 0 | 0 |

Adjuvant Agglomeration Assays

The amount of agglomeration was assessed by taking up samples from each well into 100 µl micropipettes, allowing resettling to occur for 1 hour at room temperature and then measuring the height of the sedimented gel as a percentage of the total height of the solution in the pipette. The height of the sedimented gel as a percentage of the total height of the solution in the pipette was expressed as % gel volume. The greater the % gel volume, the more structurally intact is the adjuvant.

Results and Discussion

Figure 2:
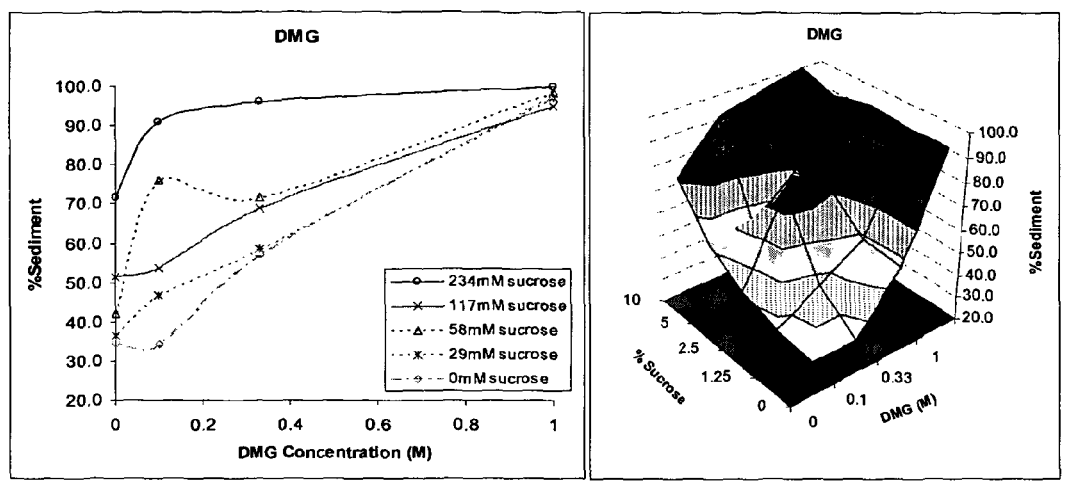
FIG. 2 shows the results of an adjuvant agglomeration assay after freezing an aluminium hydroxide gel in the presence of various concentrations of sucrose and dimethylglycine (DMG) in Example 1.

Results from these studies are shown in two forms in FIG. 2. Firstly simple XY scatter plots are shown and this is complimented by 3D sheet plots.

In the absence of any DMG or sucrose, only a 30% recovery of adjuvant was measured indicating a very significant loss in adjuvant structure had occurred during freeze thaw (~70% loss). Increasing the concentration of sucrose in the formulation increased the recovery of adjuvant to a maximum of ~70% at the highest concentration tested (234 mM, approx 8% w/v).

Increasing the concentration of DMG alone increased the recovery of adjuvant. A good dose dependent response was observed and it was possible to achieve near 100% recovery with DMG alone.

Coformulation of the adjuvant with both DMG and sucrose significantly reduced the amount of DMG required to achieve near 100% recovery.

Example 2

Methods

The aluminium hydroxide adjuvant was obtained from Sigma (A8222) as a 13 mg/ml solution at pH 6.8. Initially, 50 μl volumes of the aluminium hydroxide adjuvant were added to 100 μl volumes of sucrose and/or a further excipient diluted in Dulbecco's phosphate buffered saline (PBS) in wells of 96 well flat bottomed microplates. The further excipients were S-methyl-L-methionine, MSM and TMG. The adjuvants were frozen at −20° C. A list of final concentrations of sucrose and the further excipient before freezing can be seen in Table 2 below.

After approximately 18 hours samples containing Al(OH)$_3$ were thawed and assessed for sediment levels as described using the adjuvant agglomeration assay in Example 1.

TABLE 2

| Further excipient | Concentration (M) of further excipient | Sucrose concentration (mM) |
|---|---|---|
| S-Methyl-L-methionine | 1 | 234 |
| S-Methyl-L-methionine | 0.33 | 234 |
| S-Methyl-L-methionine | 0.1 | 234 |
| S-Methyl-L-methionine | 0 | 234 |
| S-Methyl-L-methionine | 1 | 117 |
| S-Methyl-L-methionine | 0.33 | 117 |
| S-Methyl-L-methionine | 0.1 | 117 |
| S-Methyl-L-methionine | 0 | 117 |
| S-Methyl-L-methionine | 1 | 58 |
| S-Methyl-L-methionine | 0.33 | 58 |
| S-Methyl-L-methionine | 0.1 | 58 |
| S-Methyl-L-methionine | 0 | 58 |
| S-Methyl-L-methionine | 1 | 29 |
| S-Methyl-L-methionine | 0.33 | 29 |
| S-Methyl-L-methionine | 0.1 | 29 |
| S-Methyl-L-methionine | 0 | 29 |
| S-Methyl-L-methionine | 1 | 0 |
| S-Methyl-L-methionine | 0.33 | 0 |
| S-Methyl-L-methionine | 0.1 | 0 |
| S-Methyl-L-methionine | 0 | 0 |
| MSM | 0.53 | 234 |
| MSM | 0.26 | 234 |
| MSM | 0.13 | 234 |
| MSM | 0.07 | 234 |
| MSM | 0 | 234 |
| MSM | 0.53 | 117 |
| MSM | 0.26 | 117 |
| MSM | 0.13 | 117 |
| MSM | 0.07 | 117 |
| MSM | 0 | 117 |
| MSM | 0.53 | 58 |
| MSM | 0.26 | 58 |
| MSM | 0.13 | 58 |
| MSM | 0.07 | 58 |
| MSM | 0 | 58 |
| MSM | 0.53 | 29 |
| MSM | 0.26 | 29 |
| MSM | 0.13 | 29 |
| MSM | 0.07 | 29 |
| MSM | 0 | 29 |
| MSM | 0.53 | 0 |
| MSM | 0.26 | 0 |
| MSM | 0.13 | 0 |
| MSM | 0.07 | 0 |
| MSM | 0 | 0 |
| TMG | 1 | 234 |
| TMG | 0.33 | 234 |
| TMG | 0.1 | 234 |
| TMG | 0 | 234 |
| TMG | 1 | 117 |
| TMG | 0.33 | 117 |
| TMG | 0.1 | 117 |
| TMG | 0 | 117 |
| TMG | 1 | 58 |
| TMG | 0.33 | 58 |
| TMG | 0.1 | 58 |
| TMG | 0 | 58 |
| TMG | 1 | 29 |
| TMG | 0.33 | 29 |
| TMG | 0.1 | 29 |
| TMG | 0 | 29 |
| TMG | 1 | 0 |
| TMG | 0.33 | 0 |
| TMG | 0.1 | 0 |
| TMG | 0 | 0 |

Results and Discussion

Figure 3:
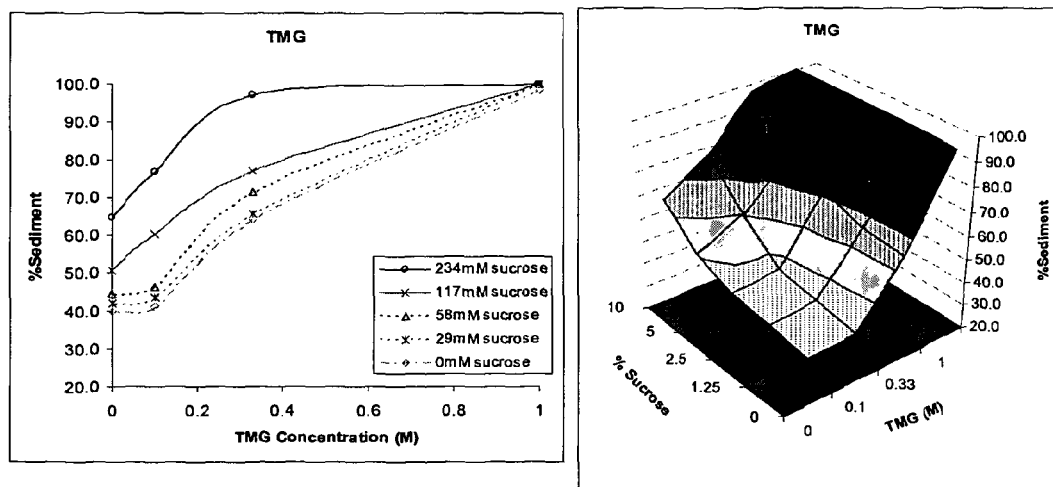
FIG. 3 shows recovery of adjuvant (Al(OH)$_3$) after freeze-thaw in the formulations described in Example 2 containing sucrose and/or trimethylglycine (TMG) as assessed using an agglomeration assay.
Figure 4:
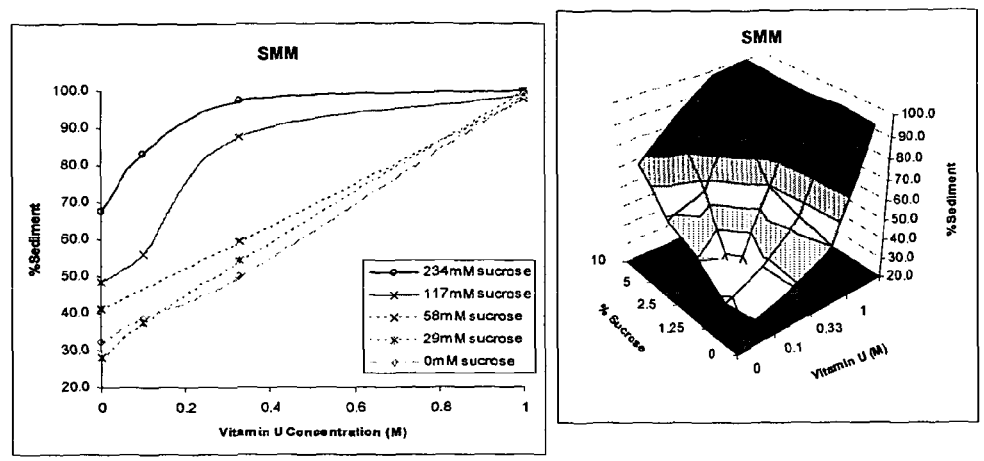
FIG. 4 shows recovery of adjuvant (Al(OH)$_3$) after freeze-thaw in the formulations described in Example 2 containing sucrose and/or S-methyl-L-methionine (SMM) or methylsulfonylmethane (MSM) as assessed by an agglomeration assay.
Figure 4:
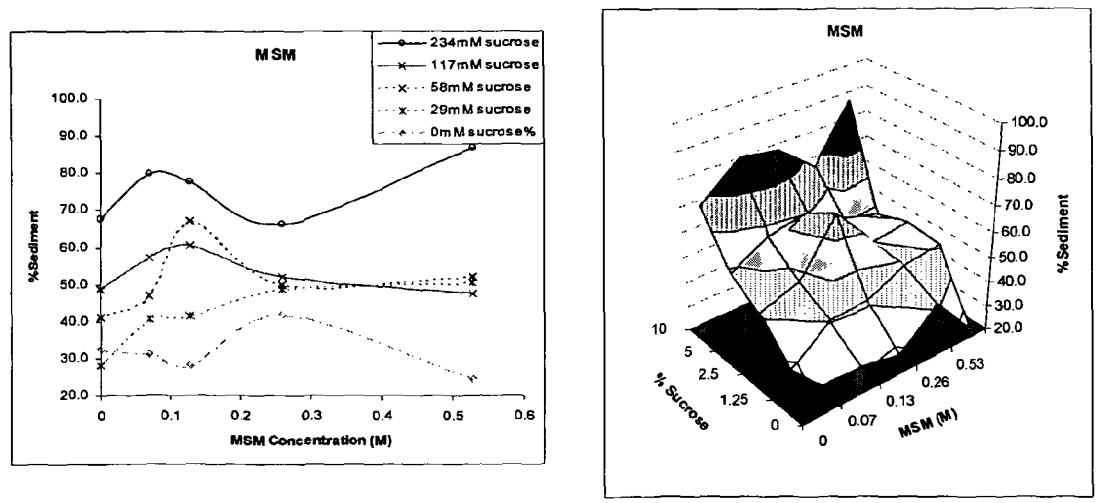

Results from these studies are shown in two forms in FIGS. 3 and 4. Firstly simple XY scatter plots are shown and this is complimented by 3D sheet plots.

In the absence of both sucrose and a further excipient only a 30% recovery of adjuvant was measured, indicating a very significant loss in adjuvant structure had occurred during freeze thaw (~70% loss). Increasing the concentration of sucrose in the formulation increased the recovery of adjuvant to a maximum of ~70% at the top concentration tested (234 mM, approx 8% w/v).

Increasing the concentration of the further excipient alone (TMG and S-Methyl-L-methionine) increased the recovery of adjuvant. In each of these cases, a good dose dependent response was observed and it was possible to achieve near 100% recovery with the further excipient alone.

Coformulation of the adjuvant with both sucrose and one of the further excipients (TMG or S-Methyl-L-methionine) significantly reduced the amount of the further excipient required to achieve near 100% recovery.

Example 3

Methods

The aluminium hydroxide adjuvant was obtained from Sigma (A8222) as a 13 mg/ml solution at pH 6.8. A volume of adjuvant was centrifuged to form a pellet which was subsequently washed in 40 mM HEPES+25 mM NaCl at pH 7.9 (twice) and re-suspended in half the original volume, resulting in an approximately 26 mg/ml solution. Into each vial was added 75 μl of 26 mg/ml adjuvant solution and 225 μl of relevant excipient (adjusted in concentration to account for added adjuvant volume) to equal the appropriate concentration, with each vial containing a final adjuvant concentration of 6.5 mg/ml. A list of final concentrations of excipients are set out in Table 4 below.

Samples were freeze dried by the VirTis Advantage freeze dryer, using the drying cycles shown in Table 3 below, lasting for approximately 3 days. Samples were frozen at −40° C. for 2 hours before a vacuum was applied, initially at 300 milli-Torre with a Thermo Savant VLP pump (Thermofisher, UK). Shelf temperature and vacuum were adjusted throughout the process and the condenser was maintained at −80° C. Step 11 was extended until the samples were stoppered before releasing the vacuum.

In the primary drying phase the shelf temperature was dropped to −45° C. The secondary drying phase included series of hold steps increasing in temperature up to 30° C. until the drying was completed. Probes recorded shelf temperatures and condenser temperatures.

TABLE 3

| Step | Shelf temp (° C.) | Time (mins) | Ramp/Hold | Vacuum (milliTorre) |
|---|---|---|---|---|
| 1 | −45 | 15 | H | — |
| 2 | −34 | 30 | R | 300 |
| 3 | −34 | 1200 | H | 300 |
| 4 | −20 | 120 | H | 300 |
| 5 | −10 | 120 | H | 300 |
| 6 | 0 | 120 | H | 300 |
| 7 | 10 | 120 | H | 80 |
| 8 | 20 | 120 | H | 80 |
| 9 | 30 | 1255 | H | 80 |
| 10 | 30 | 905 | H | 80 |
| 11 | 4 | 1255 | H | 80 |

Adjuvant Agglomeration Assays

The vials containing freeze-dried adjuvant were reconstituted into 300 μl of purified water and vortexed. The amount of agglomeration was assessed by taking up samples from each well into 100 μl micropipettes, allowing resettling to occur for 90 minutes at room temperature and then measuring the height of the sedimented gel as a percentage of the total height of the solution in the pipette. The height of the sedimented gel as a percentage of the total height of the solution in the pipette was expressed as % gel volume. The greater the % gel volume, the more structurally intact is the adjuvant.

TABLE 4

| Further excipient | Conc. (mM) of further excipient | Conc. (mM) of sucrose | % gel volume |
|---|---|---|---|
| None | 0 | 500 | 100 |
| None | 0 | 334 | 93.2 |
| None | 0 | 167 | 47.3 |
| None | 0 | 84.2 | 32.3 |
| None | 0 | 1 | 14.7 |
| None | 0 | 0 | 16.7 |
| DMG | 1 | 500 | 99.6 |
| DMG | 1 | 1 | 12.4 |
| DMG | 500 | 1 | 99.7 |
| DMG | 1 | 334 | 96.2 |
| DMG | 167 | 334 | 100 |
| DMG | 1 | 167 | 37.2 |
| DMG | 167 | 167 | 99.7 |
| DMG | 334 | 167 | 100 |
| DMG | 167 | 1 | 79.82 |
| DMG | 334 | 1 | 99.5 |
| DMG | 84 | 334 | 99.6 |
| DMG | 84 | 84 | 50.4 |
| DMG | 334 | 84 | 59.5 |
| DMG | 1 | 500 | 99.6 |
| DMG | 1 | 1 | 18.1 |
| DMG | 500 | 1 | 100 |
| DMG | 167 | 167 | 100 |
| TMG | 1 | 500 | 99.6 |
| TMG | 1 | 1 | 13.5 |
| TMG | 500 | 1 | 99.3 |
| TMG | 1 | 334 | 93.0 |
| TMG | 167 | 334 | 100 |
| TMG | 1 | 167 | 39.8 |
| TMG | 167 | 167 | 99.6 |
| TMG | 334 | 167 | 100 |
| TMG | 167 | 1 | 60.9 |
| TMG | 334 | 1 | 84.7 |
| TMG | 84 | 334 | 90.4 |
| TMG | 84 | 84 | 51.2 |
| TMG | 334 | 84 | 94.1 |
| TMG | 1 | 500 | 100 |
| TMG | 1 | 1 | 14.1 |
| TMG | 500 | 1 | 99.5 |
| TMG | 167 | 167 | 100 |
| SMM | 1 | 500 | 100 |
| SMM | 1 | 1 | 13.7 |
| SMM | 500 | 1 | 100 |
| SMM | 1 | 334 | 95.4 |
| SMM | 167 | 334 | 98.1 |
| SMM | 1 | 167 | 40.0 |
| SMM | 167 | 167 | 100 |
| SMM | 334 | 167 | 100 |
| SMM | 167 | 1 | 98.0 |
| SMM | 334 | 1 | 100 |
| SMM | 84 | 334 | 100 |
| SMM | 84 | 84 | 99.6 |
| SMM | 334 | 84 | 99.2 |
| SMM | 1 | 500 | 98.2 |
| SMM | 1 | 1 | 14.9 |
| SMM | 500 | 1 | 100 |
| SMM | 167 | 167 | 100 |
| Sarcosine | 1 | 500 | 98.1 |
| Sarcosine | 1 | 1 | 13.8 |
| Sarcosine | 500 | 1 | 100 |
| Sarcosine | 1 | 334 | 91.3 |
| Sarcosine | 167 | 334 | 98.2 |
| Sarcosine | 1 | 167 | 40.6 |
| Sarcosine | 167 | 167 | 98.5 |
| Sarcosine | 334 | 167 | 100 |
| Sarcosine | 167 | 1 | 50.7 |
| Sarcosine | 334 | 1 | 100 |
| Sarcosine | 84 | 334 | 97.2 |
| Sarcosine | 84 | 84 | 65.9 |
| Sarcosine | 334 | 84 | 100 |
| Sarcosine | 1 | 500 | 98.1 |
| Sarcosine | 1 | 1 | 14.1 |
| Sarcosine | 500 | 1 | 100 |
| Sarcosine | 167 | 167 | 98.4 |

Results and Discussion

Figure 5:
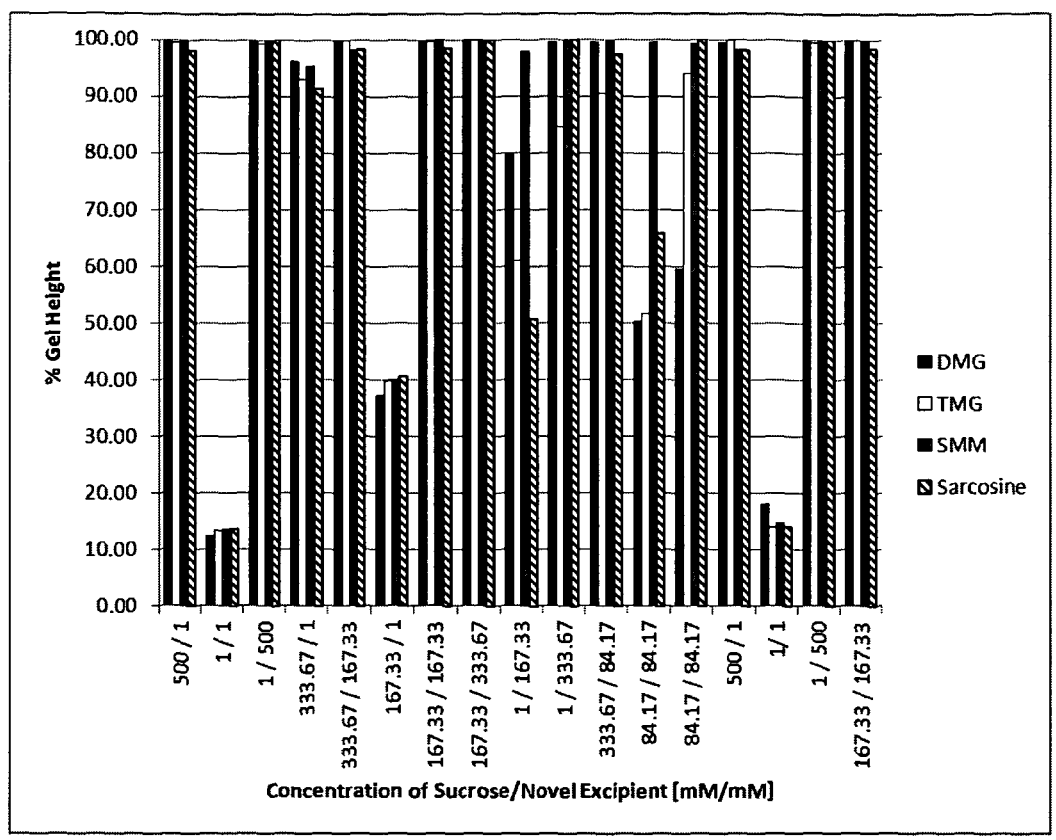
FIG. 5 shows results of an adjuvant agglomeration assay after freeze-drying of an aluminium hydroxide gel in the presence of various concentrations of sucrose and dimethylglycine (DMG), trimethylglycine (TMG), S-methyl methionine (SMM) or sarcosine in Example 3.

The results are set out in Table 4 above and graphically in FIG. 5. These confirm that adjuvant structure can be maintained upon freeze-drying adjuvant solutions in the presence of a range of concentrations of (i) DMG, TMG, S-methyl methionine or sarcosine, and (ii) sucrose. Generally, the cake quality is better for lower concentrations of the further excipient and higher concentrations of sucrose.

Example 4

Materials and Equipment

| Mannitol: | Sigma | Lot #: 077K0166 |
|---|---|---|
| DMG: | Sigma | Lot # 077K0166 |
| TMG | Sigma | Lot# 049K1529 |
| SMM | Sigma | Lot # 001425374 |
| Sarcosine | Sigma | Lot # 078K3727 |
| Aluminium Hydroxide Gel | Sigma | Lot # 018K0761 |
| Virtis Advantage Plus Freeze-Dryer: | Virtis | EQP # 084 |
| Purified Water: | Sigma | Lot # RNBB2958 |
| Micropipettes (capillary tubes): | Blaubrand, | Lot # 7091 44 |

-continued

| Freeze Drying Vials: | Adelphi 2 ml VCDIN2R |
|---|---|
| Stoppers: | Adelphi FDW13 13 mm |

Methods

Taking into account the 75 μl of adjuvant added per 300 μl freeze dry vial (¼ volume, therefore 25% more concentrated) the following excipient mixes were created in HEPES buffer as 10 ml master mixes:

TABLE 5

| | Mannitol [M] | | | | |
|---|---|---|---|---|---|
| | 0.548 | 0.274 | 0.137 | 0.069 | 0% |
| Excipient [mM] | | | 500 | | |
| | | | 250 | | |
| | | | 125 | | |
| | | | 62.5 | | |
| | | | 31.25 | | |
| | | | 15.63 | | |
| | | | 0 | | |

To each vial was added 75 μl of 26 mg/ml aluminium hydroxide adjuvant (which was prepared by centrifuging 13 mg/ml aluminium hydroxide gel and resuspending the pellet in half the original volume) and 225 μl of appropriate excipient mix, as listed above. The vials were then stoppered before placing in the VirTis Advantage freeze dryer, using the drying cycles shown in Table 6 below.

TABLE 6

| Step | Temperature (° C.) | Time (minutes) | Vacuum (MTorr) |
|---|---|---|---|
| 1 | −40 | 45 | 500 |
| 2 | −36 | 600 | 200 |
| 3 | −20 | 120 | 300 |
| 4 | −10 | 120 | 300 |
| 5 | 0 | 120 | 300 |
| 6 | 10 | 120 | 80 |
| 7 | 20 | 120 | 80 |
| 8 | 30 | 1255 | 80 |
| 9 | 4 | 1255 | 80 |

Table 6

After freeze drying the vials were stoppered under vacuum, capped and photographs were taken. Adjuvant agglomeration was assessed as set out in Example 3.

Results and Discussion

The results are set out in Table 7 to 10 below.

TABLE 7A

| Mannitol [M] | 0.548 | 0.548 | 0.548 | 0.548 | 0.548 | 0.548 | 0.548 |
|---|---|---|---|---|---|---|---|
| DMG [mM] | 500 | 250 | 125 | 62.5 | 31.25 | 15.625 | 0 |
| % Gel height | 100 | 100 | 100 | 100 | 98 | 97 | 98.5 |

TABLE 7B

| Mannitol [M] | 0.274 | 0.274 | 0.274 | 0.274 | 0.274 | 0.274 | 0.274 |
|---|---|---|---|---|---|---|---|
| DMG [mM] | 500 | 250 | 125 | 62.5 | 31.25 | 15.625 | 0 |
| % Gel height | 100 | 100 | 100 | 98 | 77.5 | 96 | 50 |

TABLE 7C

| Mannitol [M] | 0.137 | 0.137 | 0.137 | 0.137 | 0.137 | 0.137 | 0.137 |
|---|---|---|---|---|---|---|---|
| DMG [mM] | 500 | 250 | 125 | 62.5 | 31.25 | 15.625 | 0 |
| % Gel height | 98 | 100 | 96 | 73.3 | 43.75 | 46.2 | 32.5 |

TABLE 7D

| Mannitol [M] | 0.069 | 0.069 | 0.069 | 0.069 | 0.069 | 0.069 | 0.069 |
|---|---|---|---|---|---|---|---|
| DMG [mM] | 500 | 250 | 125 | 62.5 | 31.25 | 15.625 | 0 |
| % Gel height | 100 | 100 | 90 | 28.6 | 26.2 | 21.2 | 16.7 |

TABLE 7E

| Mannitol [M] | 0.041 | 0.041 | 0.041 | 0.041 | 0.041 | 0.041 | 0.041 |
|---|---|---|---|---|---|---|---|
| DMG [mM] | 500 | 250 | 125 | 62.5 | 31.25 | 15.625 | 0 |
| % Gel height | 99 | 99 | 90 | 42.5 | 27.0 | 18.8 | 12.5 |

TABLE 7F

| Mannitol [M] | 0.0206 | 0.0206 | 0.0206 | 0.0206 | 0.0206 | 0.0206 | 0.0206 |
|---|---|---|---|---|---|---|---|
| DMG [mM] | 500 | 250 | 125 | 62.5 | 31.25 | 15.625 | 0 |
| % Gel height | 99 | 98 | 95 | 41.5 | 25.0 | 14.0 | 12.5 |

TABLE 7G

| Mannitol M | 0 | 0 | 0 | 0 | 0 | 0 | 0 |
|---|---|---|---|---|---|---|---|
| DMG [mM] | 500 | 250 | 125 | 62.5 | 31.25 | 15.625 | 0 |
| % Gel height | 100 | 97 | 80 | 31.6 | 18.6 | 13.6 | 11.8 |

TABLE 8A

| Mannitol M | 0.548 | 0.548 | 0.548 | 0.548 | 0.548 | 0.548 | 0.548 |
|---|---|---|---|---|---|---|---|
| TMG [mM] | 500 | 250 | 125 | 62.5 | 31.25 | 15.625 | 0 |
| % Gel height | 100 | 100 | 100 | 100 | 97 | 94 | 92 |

TABLE 8B

| Mannitol M | 0.274 | 0.274 | 0.274 | 0.274 | 0.274 | 0.274 | 0.274 |
|---|---|---|---|---|---|---|---|
| TMG [mM] | 500 | 250 | 125 | 62.5 | 31.25 | 15.625 | 0 |
| % Gel height | 100 | 100 | 100 | 100 | 88.9 | 80 | 45 |

TABLE 8C

| Mannitol M | 0.137 | 0.137 | 0.137 | 0.137 | 0.137 | 0.137 | 0.137 |
|---|---|---|---|---|---|---|---|
| TMG [mM] | 500 | 250 | 125 | 62.5 | 31.25 | 15.625 | 0 |
| % Gel height | 100 | 98 | 87.5 | 50 | 50 | 38.6 | 35.7 |

TABLE 8D

| Mannitol M | 0.069 | 0.069 | 0.069 | 0.069 | 0.069 | 0.069 | 0.069 |
|---|---|---|---|---|---|---|---|
| TMG [mM] | 500 | 250 | 125 | 62.5 | 31.25 | 15.625 | 0 |
| % Gel height | 99 | 98 | 90 | 50 | 25 | 15.8 | 11.6 |

TABLE 8E

| Mannitol M | 0.041 | 0.041 | 0.041 | 0.041 | 0.041 | 0.041 | 0.041 |
|---|---|---|---|---|---|---|---|
| TMG [mM] | 500 | 250 | 125 | 62.5 | 31.25 | 15.625 | 0 |
| % Gel height | 100 | 100 | 98 | 50 | 25.0 | 15.8 | 11.6 |

TABLE 8F

| Mannitol M | 0.0206 | 0.0206 | 0.0206 | 0.0206 | 0.0206 | 0.0206 | 0.0206 |
|---|---|---|---|---|---|---|---|
| TMG [mM] | 500 | 250 | 125 | 62.5 | 31.25 | 15.625 | 0 |
| % Gel height | 98 | 96 | 80 | 44.0 | 20.0 | 16.6 | 13.5 |

TABLE 8G

| Mannitol M | 0 | 0 | 0 | 0 | 0 | 0 | 0 |
|---|---|---|---|---|---|---|---|
| TMG [mM] | 500 | 250 | 125 | 62.5 | 31.25 | 15.625 | 0 |
| % Gel height | 98 | 90 | 50 | 27.7 | 15.5 | 10.7 | 9.9 |

TABLE 9A

| Mannitol M | 0.548 | 0.548 | 0.548 | 0.548 | 0.548 | 0.548 | 0.548 |
|---|---|---|---|---|---|---|---|
| SMM [mM] | 500 | 250 | 125 | 62.5 | 31.25 | 15.625 | 0 |
| % Gel height | 100 | 100 | 100 | 98 | 95 | 100 | 95.0 |

TABLE 9B

| Mannitol M | 0.274 | 0.274 | 0.274 | 0.274 | 0.274 | 0.274 | 0.274 |
|---|---|---|---|---|---|---|---|
| SMM [mM] | 500 | 250 | 125 | 62.5 | 31.25 | 15.625 | 0 |
| % Gel height | 100 | 100 | 100 | 100 | 100 | 90 | 48 |

TABLE 9C

| Mannitol M | 0.137 | 0.137 | 0.137 | 0.137 | 0.137 | 0.137 | 0.137 |
|---|---|---|---|---|---|---|---|
| SMM [mM] | 500 | 250 | 125 | 62.5 | 31.25 | 15.625 | 0 |
| % Gel height | 98 | 100 | 98 | 98 | 62.5 | 50 | 31.9 |

TABLE 9D

| Mannitol M | 0.069 | 0.069 | 0.069 | 0.069 | 0.069 | 0.069 | 0.069 |
|---|---|---|---|---|---|---|---|
| SMM [mM] | 500 | 250 | 125 | 62.5 | 31.25 | 15.625 | 0 |
| % Gel height | 100 | 97 | 100 | 88.2 | 27.5 | 23.4 | 18.75 |

TABLE 9E

| Mannitol M | 0.041 | 0.041 | 0.041 | 0.041 | 0.041 | 0.041 | 0.041 |
|---|---|---|---|---|---|---|---|
| SMM [mM] | 500 | 250 | 125 | 62.5 | 31.25 | 15.625 | 0 |
| % Gel height | 100 | 100 | 97 | 97 | 78.6 | 24.7 | 15.7 |

TABLE 9F

| Mannitol M | 0.0206 | 0.0206 | 0.0206 | 0.0206 | 0.0206 | 0.0206 | 0.0206 |
|---|---|---|---|---|---|---|---|
| SMM [mM] | 500 | 250 | 125 | 62.5 | 31.25 | 15.625 | 0 |
| % Gel height | 98 | 98 | 90 | 98 | 45 | 23.8 | 12.5 |

TABLE 9G

| Mannitol M | 0 | 0 | 0 | 0 | 0 | 0 | 0 |
|---|---|---|---|---|---|---|---|
| SMM [mM] | 500 | 250 | 125 | 62.5 | 31.25 | 15.625 | 0 |
| % Gel height | 100 | 100 | 100 | 96 | 34.4 | 26.2 | 11.1 |

TABLE 10A

| Mannitol M | 0.548 | 0.548 | 0.548 | 0.548 | 0.548 | 0.548 | 0.548 |
|---|---|---|---|---|---|---|---|
| Sarc. [mM] | 500 | 250 | 125 | 62.5 | 31.25 | 15.625 | 0 |
| % Gel height | 100 | 100 | 97 | 88 | 97 | 88 | 89 |

TABLE 10B

| Mannitol M | 0.274 | 0.274 | 0.274 | 0.274 | 0.274 | 0.274 | 0.274 |
|---|---|---|---|---|---|---|---|
| Sarc. [mM] | 500 | 250 | 125 | 62.5 | 31.25 | 15.625 | 0 |
| % Gel height | 100 | 100 | 100 | 98 | 87.5 | 88.9 | 39.8 |

TABLE 10C

| Mannitol M | 0.137 | 0.137 | 0.137 | 0.137 | 0.137 | 0.137 | 0.137 |
|---|---|---|---|---|---|---|---|
| Sarc. [mM] | 500 | 250 | 125 | 62.5 | 31.25 | 15.625 | 0 |
| % Gel height | 98 | 100 | 61.2 | 40 | 35.7 | 33.7 | 30.8 |

TABLE 10D

| Mannitol M | 0.069 | 0.069 | 0.069 | 0.069 | 0.069 | 0.069 | 0.069 |
|---|---|---|---|---|---|---|---|
| Sarc. [mM] | 500 | 250 | 125 | 62.5 | 31.25 | 15.625 | 0 |
| % Gel height | 100 | 100 | 98 | 34.1 | 22.7 | 21.9 | 20.4 |

TABLE 10E

| Mannitol M | 0.041 | 0.041 | 0.041 | 0.041 | 0.041 | 0.041 | 0.041 |
|---|---|---|---|---|---|---|---|
| Sarc. [mM] | 500 | 250 | 125 | 62.5 | 31.25 | 15.625 | 0 |
| % Gel height | 100 | 100 | 98 | 28.6 | 20 | 14.8 | 13.1 |

TABLE 10F

| Mannitol M | 0.0206 | 0.0206 | 0.0206 | 0.0206 | 0.0206 | 0.0206 | 0.0206 |
|---|---|---|---|---|---|---|---|
| Sarc. [mM] | 500 | 250 | 125 | 62.5 | 31.25 | 15.625 | 0 |
| % Gel height | 97 | 97 | 80 | 38 | 20 | 13.5 | 12.6 |

TABLE 10G

| Mannitol M | 0 | 0 | 0 | 0 | 0 | 0 | 0 |
|---|---|---|---|---|---|---|---|
| Sarc. [mM] | 500 | 250 | 125 | 62.5 | 31.25 | 15.625 | 0 |
| % Gel height | 100 | 100 | 90 | 37.5 | 17.7 | 12.8 | 11.1 |

These results show the presence of DMG, TMG, SMM and sarcosine allows for reduction in the concentration of sugars without a reduction of adjuvant protection. This demonstrates the clear role of excipients in adjuvant stabilisation.

Example 5

Materials and Equipment

| Mannitol: | Sigma | Lot #: 077K0166 |
|---|---|---|
| DMG: | Sigma | Lot # 077K0166 |
| TMG | Sigma | Lot# 049K1529 |
| SMM | Sigma | Lot # 001425374 |
| Sarcosine | Sigma | Lot # 078K3727 |
| Aluminium Hydroxide Gel | Sigma | Lot # 018K0761 |
| Virtis Advantage Plus Freeze-Dryer: | Virtis | EQP # 084 |
| Purified Water: | Sigma | Lot # RNBB2958 |
| Micropipettes (capillary tubes): | Blaubrand, | Lot # 7091 44 |
| Freeze Drying Vials: | Adelphi 2 ml VCDIN2R | |
| Stoppers: | Adelphi FDW13 13 mm | |

Methods

Taking into account the 75 µl of adjuvant added per 300 µl freeze dry vial (¼ volume, therefore 25% more concentrated) the following excipient mixes were created in HEPES buffer in 10 ml master mixes:

TABLE 11

|  | Mannitol [M] | | | | | |
|---|---|---|---|---|---|---|
|  | 0.767 | 0.657 | 0.548 | 0.438 | 0.329 | 0 |
| Excipient [M] | | | 1.4 | | | |
| | | | 1.2 | | | |
| | | | 1.0 | | | |
| | | | 0.8 | | | |
| | | | 0.6 | | | |
| | | | 0 | | | |

To each vial was added 75 µl of 26 mg/ml aluminium hydroxide adjuvant (which was prepared by centrifuging 13 mg/ml aluminium hydroxide gel and resuspending the pellet in half the original volume) and 225 µl of appropriate excipient mix, as listed above. The vials were then stoppered before placing in the freeze drier and run on the cycle set out in Table 12.

TABLE 12

| Step | Temperature (° C.) | Time (minutes) | Vacuum (MTorr) |
|---|---|---|---|
| 1 | −40 | 45 | |
| 2 | −36 | 600 | 200 |
| 3 | −20 | 120 | 300 |
| 4 | −10 | 120 | 300 |
| 5 | 0 | 120 | 300 |
| 6 | 10 | 120 | 80 |
| 7 | 20 | 120 | 80 |
| 8 | 30 | 1255 | 80 |
| 9 | 4 | 1255 | 80 |

After freeze drying the vials were stoppered under vacuum, capped and photographs were taken. Adjuvant agglomeration was assessed as set out in Example 3.

Results and Discussion

The results are set out in Table 13 and 14 below.

TABLE 13

| Mannitol [M] | Excipient Type/ Concentration [mM] | % Protection |
|---|---|---|
| 0.767 | DMG 1.4M | 100 |
| | 1.2M | 100 |
| | 1.0M | 100 |
| | 0.8M | 100 |
| | 0.6M | 100 |
| | 0M | 86 |
| 0.657 | DMG 1.4M | 100 |
| | 1.2M | 100 |

TABLE 13-continued

| Mannitol [M] | Excipient Type/Concentration [mM] | % Protection |
|---|---|---|
| | 1.0M | 100 |
| | 0.8M | 100 |
| | 0.6M | 100 |
| | 0M | 75 |
| 0.548 | DMG 1.4M | 100 |
| | 1.2M | 100 |
| | 1.0M | 100 |
| | 0.8M | 100 |
| | 0.6M | 100 |
| | 0M | 63 |
| 0.438 | DMG 1.4M | 100 |
| | 1.2M | 100 |
| | 1.0M | 96 |
| | 0.8M | 100 |
| | 0.6M | 100 |
| | 0M | 50 |
| 0.329 | DMG 1.4M | 100 |
| | 1.2M | 100 |
| | 1.0M | 100 |
| | 0.8M | 96 |
| | 0.6M | 100 |
| | 0M | 23 |
| 0 | DMG 1.4M | 100 |
| | 1.2M | 100 |
| | 1.0M | 100 |
| | 0.8M | 96 |
| | 0.6M | 96 |
| | 0M | 11 |
| 0.767 | TMG 1.4M | 100 |
| | 1.2M | 100 |
| | 1.0M | 100 |
| | 0.8M | 100 |
| | 0.6M | 100 |
| | 0M | 90 |
| 0.657 | TMG 1.4M | 100 |
| | 1.2M | 100 |
| | 1.0M | 100 |
| | 0.8M | 98 |
| | 0.6M | 100 |
| | 0M | 80 |
| 0.548 | TMG 1.4M | 100 |
| | 1.2M | 100 |
| | 1.0M | 100 |
| | 0.8M | 100 |
| | 0.6M | 100 |
| | 0M | 70 |
| 0.438 | TMG 1.4M | 100 |
| | 1.2M | 100 |
| | 1.0M | 100 |
| | 0.8M | 100 |
| | 0.6M | 100 |
| | 0M | 50 |
| 0.329 | TMG 1.4M | 100 |
| | 1.2M | 100 |
| | 1.0M | 100 |
| | 0.8M | 96 |
| | 0.6M | 100 |
| | 0M | 50 |
| 0 | TMG 1.4M | 100 |
| | 1.2M | 100 |
| | 1.0M | 100 |
| | 0.8M | 100 |
| | 0.6M | 96 |
| | 0M | 14 |

TABLE 14

| Mannitol [M] | Excipient Type/Concentration [mM] | % Protection |
|---|---|---|
| 0.767 | SMM 1.4M | 100 |
| | 1.2M | 100 |
| | 1.0M | 98 |
| | 0.8M | 98 |
| | 0.6M | 98 |
| | 0M | 82 |
| 0.657 | SMM 1.4M | 100 |
| | 1.2M | 98 |
| | 1.0M | 98 |
| | 0.8M | 98 |
| | 0.6M | 100 |
| | 0M | 75 |
| 0.548 | SMM 1.4M | 100 |
| | 1.2M | 100 |
| | 1.0M | 100 |
| | 0.8M | 100 |
| | 0.6M | 100 |
| | 0M | 68 |
| 0.438 | SMM 1.4M | 100 |
| | 1.2M | 100 |
| | 1.0M | 100 |
| | 0.8M | 100 |
| | 0.6M | 98 |
| | 0M | 52 |
| 0.329 | SMM 1.4M | 100 |
| | 1.2M | 100 |
| | 1.0M | 100 |
| | 0.8M | 98 |
| | 0.6M | 100 |
| | 0M | 46 |
| 0 | SMM 1.4M | 100 |
| | 1.2M | 100 |
| | 1.0M | 100 |
| | 0.8M | 100 |
| | 0.6M | 95 |
| | 0M | 12 |

These results show the presence of DMG, TMG and SMM allows for reduction in the concentration of sugars without a reduction of adjuvant protection. This demonstrates the clear role of excipients in adjuvant stabilisation.

Example 6

Introduction

Bovine serum albumin (BSA) is commonly used as a model in experiments where, for example, protein adsorption onto an adjuvant is to be measured.

Materials and Equipment

| | | |
|---|---|---|
| BSA: | Sigma P5369 | Lot 058K6061 |
| Alhydrogel: 2% | Brenntag | Lot 4420 |
| Mannitol: | Sigma | Lot #: 077K0166 |
| DMG: | Sigma | Lot # 077K0166 |
| TMG: | Sigma | Lot# 049K1529 |
| SMM: | Sigma, | Lot # 001425374 |
| DPBS: | Sigma | RNBB1286 |
| Virtis Advantage Plus Freeze-Dryer: | Virtis | EQP # 084 |
| Purified Water: | Sigma | Lot # RNBB2958 |
| Freeze Drying Vials: | Adelphi 2 ml VCDIN2R | |
| Stoppers: | Adelphi FDW13 13 mm | |
| −20° C. Freezer: | Stabilitech EQP # | |
| Nunc 96-well ELISA plate | | |
| Bradford Reagent: | Sigma B6916-500ML | Batch 080M4359 |
| BioTek Plate Reader: | Stabilitech EQP: 027 | |

Protein Adsorption

Alhydrogel (supplied at 2% stock (w/v)) was added to PBS containing BSA to equal a final 10 ml volume with concentration of 0.52% Alhydrogel and 200 µg/ml BSA. The protein adsorption step was incubated by gently rocking at room temperature before placing overnight at +4° C.

The following excipient mixes were prepared in 5 ml volumes:
- 1.315 M (24%)Mannitol
- 1.315 M (24%)+1.6 M DMG
- 1.315 M (24%)+1.6 M TMG
- 1.315 M (24%)+1.6 M SMM
- 1.096 M (20%)Mannitol+1.2 M DMG
- 1.096 M (20%)+1.2 M TMG
- 1.096 M (20%)+1.2 M SMM
- 0.877 M (16%)Mannitol+0.8 M DMG
- 0.877 M (16%)+0.8 M TMG
- 0.877 M (16%)+0.8 M SMM
- PBS Adjuvant-Excipient Processing The adjuvant was mixed with the excipient concentration in a 1:1 ratio (2 ml+2 ml) to create half concentration of excipients above, 0.26% Alhydrogel and 100 µg/ml BSA. This was incubated at +4° C. for 12 hours before being split off into 300 µl volumes which were either (a) frozen (−80° C.), (b) lyophilised as set out in Table 15 below or (c) held at +4° C. as liquid.

Blanks of equivalent volumes were produced and processed as discussed where no protein was included as blanks for the protein assay.

TABLE 15

| Step | Temperature (° C.) | Time (minutes) | Vacuum (MTorr) |
| --- | --- | --- | --- |
| 1 | −40 | 45 | |
| 2 | −36 | 600 | 200 |
| 3 | −20 | 120 | 300 |
| 4 | −10 | 120 | 300 |
| 5 | 0 | 120 | 300 |
| 6 | 10 | 120 | 80 |
| 7 | 20 | 120 | 80 |
| 8 | 30 | 1255 | 80 |
| 9 | 4 | 1255 | 80 |

After freeze drying the vials were stoppered under vacuum, capped and photographs were taken and cakes were scored on cake quality were scored on cake quality as described in Example 3.

The liquid, frozen and lyophilised vials were then placed at room temperature to equilibrate/thaw whilst the lyophilised vials were reconstituted in 300 µl of purified water and vortexed until complete reconstitution was observed.

Each of the 300 µl volumes was pulsed on the microfuge for 1 minute to pellet the adjuvant, the supernatant was discarded and the pellet was resuspended in equal volumes of PBS. This procedure was repeated 3 times to completely remove residual excipients from the adjuvant.

Protein Assay (Bradford)

Each of the excipient combinations was run in duplicate with a duplicate counterpart blank (i.e. no protein). The liquid, lyophilised and frozen samples were run on separate plates. To standardise protein concentrations each plate was run with a standard curve starting with BSA at 200 µg/ml serially diluted down to 6.25 µg/ml. A volume of 50 µl of adjuvant sample was added to each well before adding 125 µl of Bradford solution (equilibrated to room temperature). The plates were transferred to the plate reader which was set on the plate shake mode (to keep adjuvant in suspension) for 5 minutes before each plate was read at an absorbance at 595 nm.

Results

For each plate standard curves were produced (with blanks subtracted) and those standard curves (with y=mx+c equation) were used to ascertain the protein concentrations of the adjuvant samples with their respective blanks also subtracted. Data was plotted as total protein concentration of the adjuvant sample/ml and also as a percentage of the PBS control.

Figure 6:
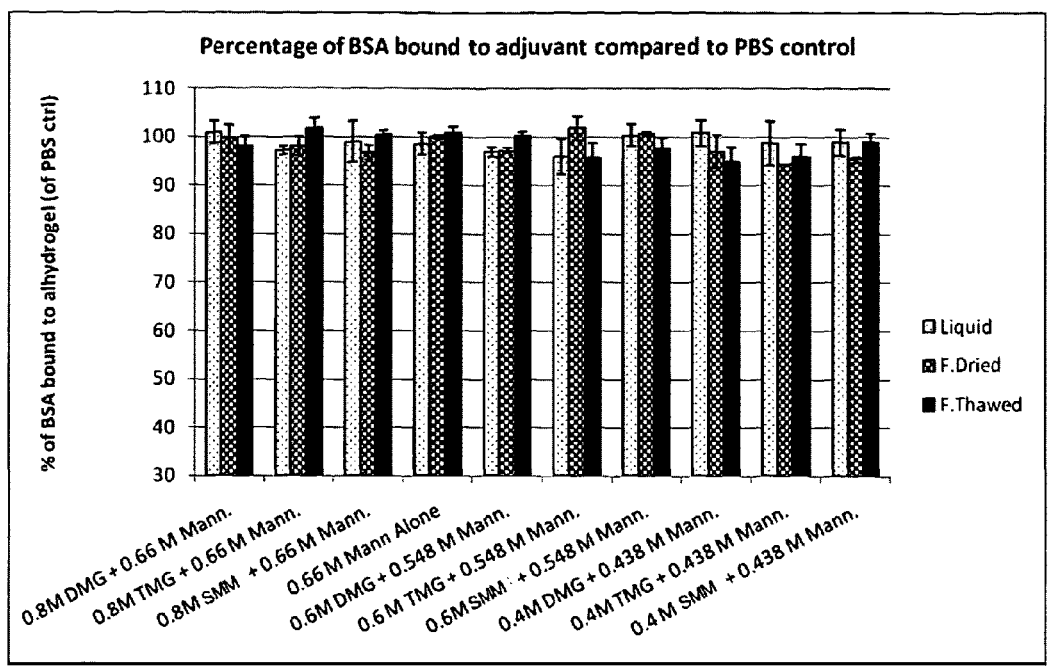
FIG. 6 shows the percentage of BSA bound to the adjuvant in Example 6 compared to the control.

The results are set out in Table 16 to 18 below and in FIGS. 6 and 7.

TABLE 16

| | Excip [M] | | | |
| --- | --- | --- | --- | --- |
| | 0.8M DMG + 0.66M Mann | 0.8M TMG + 0.66M Mann | 0.8M SMM + 0.66M Mann | 0.66M Mann |
| % BSA (of PBS Ctrl.) | 99.49 | 98.12 | 96.76 | 100.00 |

TABLE 17

| | Excip [M] | | |
| --- | --- | --- | --- |
| | 0.6M DMG + 0.548M Mann | 0.6M TMG + 0.548M Mann | 0.6M SMM + 0.548M Mann |
| % BSA (of PBS Ctrl.) | 97.27 | 101.877 | 100.68 |

TABLE 18

| | Excip [M] | | |
| --- | --- | --- | --- |
| | 0.4M DMG + 0.438M Mann | 0.4M TMG + 0.438M Mann | 0.4M SMM + 0.438M Mann |
| % BSA (of PBS Ctrl.) | 97.088 | 94.37 | 95.39 |

Discussion

These mannitol and DMG, TMG and SMM concentrations resulted in close to complete structural preservation of the adjuvant structure.

The total protein results demonstrate that BSA levels adsorbed to the adjuvant were comparable across the mannitol-excipient ranges, and indeed to mannitol alone (0.66 M/12%) and PBS. This suggests that there was no elution of the protein caused by the excipients when introduced to pre-adsorbed Alhydrogel. This was also the case for PBS and mannitol. The liquid hold, lyophilisation and incidents of freeze-thaw did not exacerbate any elution.

This experiment shows that the protein is still adsorbed to the adjuvant under conditions where the structure of the adjuvant is preserved during lyophilisation.

Example 7

Introduction

This experiment compares a mannitol base with DMG, TMG, and SMM at levels that have previously been shown to protect adjuvant structure. It compares the antigenicity of the antibody bound to the alum both when the alum antibody has been kept at 4° C. and when it has been freeze thawed, using a dot blot to probe the activity of the antibody in both storage methods.

Materials
Chemical

|  | Supplier | Product code | Lot no. |
|---|---|---|---|
| PBS x 10 |  | — | — |
| Tween 20 | Sigma | P1379 | — |
| Skimmed milk powder | Marvel | — | — |
| Alhydrogel | Brenntag | — | 4420 |
| TMB Chromogen | Invitrogen | SB02 | 727643282A |
| Mouse mAb | Serotec | 8437 | 5208x220610 |
| Anti mouse HRP | Sigma | A0412 | 077K6008 |
| Mannitol | Sigma | M1902 | 077K0166 |
| DMG | Sigma | D1156 | 077K1856U |
| TMG | Sigma | B2629 | 049K1529 |
| SMM | Sigma | 12209121 | 0001423374 |

Other

|  | Supplier | Product code | Lot no. |
|---|---|---|---|
| Nitrocellulose membrane | Sigma | N8267 | 3110 |
| Petri dish | Fisher | FB51504 | 264541 |

Equipment

|  | Manufacturer | Equipment No. |
|---|---|---|
| Rocker | Stuart Scientific | EQP#091 |
| Balance | Sartorius | EQP#089 |
| Forma 900 series −80° C. freezer | Thermofisher | EQP#015 |
| Scanner | Cannon | — |

Methods

Mouse antibody adsorbed onto alum was freeze thawed and kept at 4° C. in the presence of various excipients. This was assayed using a dot blot to see if the mouse antibody had retained its antigenicity.

2% alhydrogel solution was diluted to 0.52% with PBS and mouse antibody added to a concentration of 200 μg/ml. This was allowed to mix for an hour at room temperature with agitation then put at 4° C. over night. The alum-antibody solution was then diluted 1:1 with excipient solutions to give final excipient concentrations as listed below:

0.657M mannitol
0.657M mannitol+0.8M DMG
0.657M mannitol+0.8M TMG
0.657M mannitol+0.8M SMM
PBS These solutions were then split into two aliquots. One of each excipient was kept at 4° C., the other was stored at -80° C. until required.

Dot Blot of Retained Mouse Antibody Activity

A nitrocellulose membrane was cut to the required size and 2 μl of samples applied as dots. This was allowed to dry and then incubated in 10 ml PBS +0.05% Tween 20+5% milk for 1hour at room temperature on a rocker. This solution was then removed and the membrane then incubated in 10 ml of anti-mouse-HRP (horseradish peroxidase) diluted to 1:5000 in PBS +0.05% Tween 20+5% milk for 1 hour at room temperature on a rocker. The membranes were then washed for 3×10 minutes with PBS +0.05% Tween 20. The membranes were blotted on tissue paper to remove excess buffer and then 10 ml of TMB (tetramethylbenzidine) was put on to the membrane for 5 minutes. The TMB was then dabbed off and blot colour scanned.

Results

FIG. 8 (Table 19 shows the layout of samples tested in FIG. 8) shows that in both the liquid (FIG. 8A) and freeze-thawed (FIG. 8B) samples, all samples not containing antibody are negative as expected and the positive control of antibody only is strongly positive. In the liquid samples all the dots are similar at the same dilutions. The frozen samples are less consistent, especially between the samples in excipient and the PBS control sample. The PBS sample is weaker at the 1:500 dilution then the samples in the different excipients.

FIG. 9 (Table 20 shows the layout of samples tested in FIG. 9) shows results consistent with this. All the negative controls without antibody are negative, including the excipient only controls which show that the excipients are not interfering with the assay. The PBS samples are again weaker than the liquid samples when frozen, especially when compared to samples in excipient at 1:300 and 1:500.

TABLE 19

Figure 7:
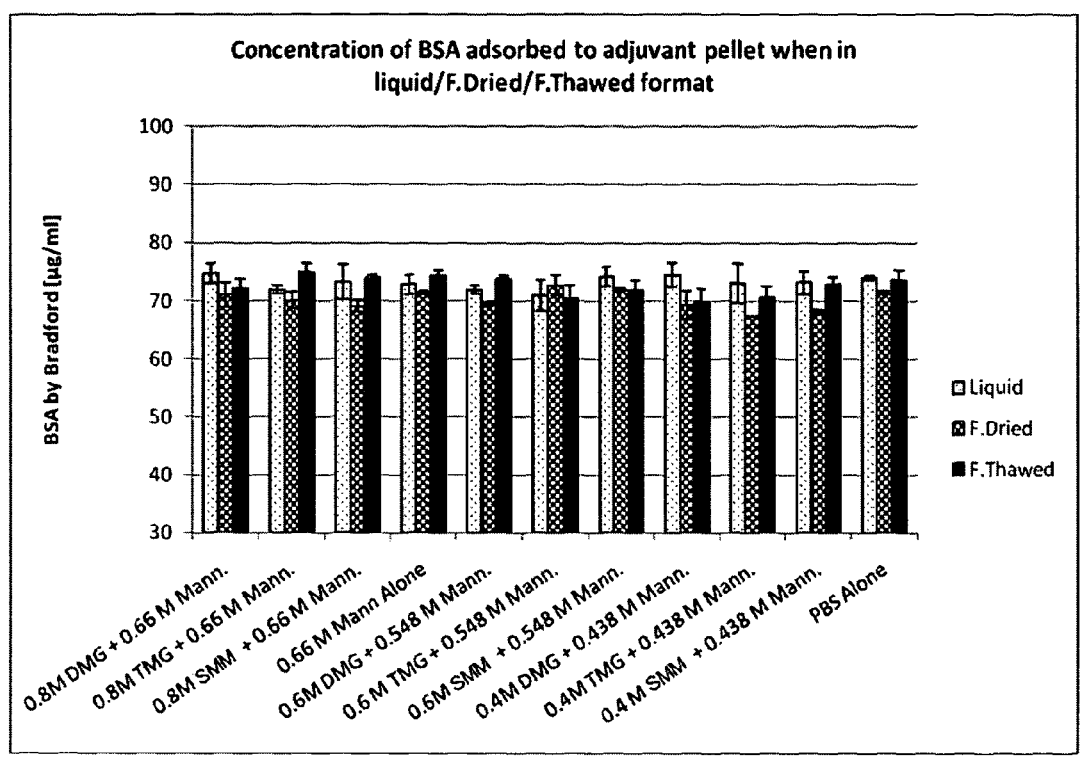
FIG. 7 shows the concentration of BSA bound to the adjuvant in Example 6.

| Layout of samples tested in FIG. 7 | | |
|---|---|---|
| 1. 0.52% alum only | 2. Mouse mAb 50 ug/ml 1:100 | 3. Mouse mAb 50 ug/ml 1:500 |
| 4. Mouse mAb-12% mannitol-0.26% alum | 5. Mouse mAb-12% mannitol-0.26% alum 1:100 | 6. Mouse mAb-12% mannitol-0.26% alum 1:500 |
| 7. Mouse mAb-12% mannitol-0.8M DMG-0.26% alum | 8. Mouse mAb-12% mannitol-0.8M DMG-0.26% alum 1:100 | 9. Mouse mAb-12% mannitol-0.8M DMG-0.26% alum 1:500 |
| 10. Mouse mAb-12% mannitol-0.8M TMG-0.26% alum | 11. Mouse mAb-12% mannitol-0.8M TMG-0.26% alum 1:100 | 12. Mouse mAb-12% mannitol-0.8M TMG-0.26% alum 1:500 |
| 13. Mouse mAb-12% mannitol-0.8M Vit U 0.26% alum | 14. Mouse mAb-12% mannitol-0.8M Vit U 0.26% alum 1:100 | 15. Mouse mAb-12% mannitol-0.8M Vit U 0.26% alum 1:500 |
| 16. Mouse mAb-PBS-0.26% alum | 17. Mouse mAb-PBS-0.26% alum 1:100 | 18. Mouse mAb-PBS-0.26% alum 1:500 |

TABLE 20

| layout of samples tested in FIG. 8 | | |
|---|---|---|
| 1. 0.52% alum only | 2. Mouse mAb 50 ug/ml | 3. 12% mannitol-0.8M Vit U 0.26% alum |
| 4. Mouse mAb-12% mannitol-0.26% alum 1:100 | 5. Mouse mAb-12% mannitol-0.26% alum 1:300 | 6. Mouse mAb-12% mannitol-0.26% alum 1:500 |
| 7. Mouse mAb-12% mannitol-0.8M DMG-0.26% alum 1:100 | 8. Mouse mAb-12% mannitol-0.8M DMG-0.26% alum 1:300 | 9. Mouse mAb-12% mannitol-0.8M DMG-0.26% alum 1:500 |
| 10. Mouse mAb-12% mannitol-0.8M TMG-0.26% alum 1:100 | 11. Mouse mAb-12% mannitol-0.8M TMG-0.26% alum 1:300 | 12. Mouse mAb-12% mannitol-0.8M TMG-0.26% alum 1:500 |
| 13. Mouse mAb-12% mannitol-0.8M Vit U 0.26% alum 1:100 | 14. Mouse mAb-12% mannitol-0.8M Vit U 0.26% alum 1:300 | 15. Mouse mAb-12% mannitol-0.8M Vit U 0.26% alum 1:500 |
| 16. Mouse mAb-PBS-0.26% alum 1:100 | 17. Mouse mAb-PBS-0.26% alum 1:300 | 18. Mouse mAb-PBS-0.26% alum 1:500 |
| 19. 12% mannitol-0.26% alum | 20. 12% mannitol-0.8M DMG-0.26% alum | 21. 12% mannitol-0.8M TMG-0.26% alum |

Conclusion

Both sets of results show weaker positive results for PBS only samples compared to samples containing excipients when frozen. This shows that the excipients are offering protection to the antibody with alum when compared to antibody with alum alone when the samples are freeze-thawed, as the antibody is retaining its antigenicity more efficiently.

The invention claimed is:

1. A method for preserving an aluminium-salt adjuvant during freezing or freeze-drying comprising freezing or freeze-drying an aqueous suspension or solution comprising:
   (a) an aluminium salt adjuvant;
   (b) a compound of formula (I) or a physiologically acceptable salt or ester thereof

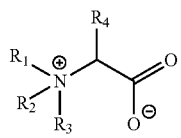

(I)

wherein:
   $R_1$ represents hydrogen or $C_{1-6}$ alkyl; and
   $R_4$ represents hydrogen; or
   $R_1$ and $R_4$ together with the atoms to which they are attached form a pyrrolidine ring;
   $R_2$ represents hydrogen, $C_{1-6}$ alkyl or —$(CH_2)_{2-5}$NHC(O)$(CH_2)_{5-15}$CH$_3$; and
   $R_3$ represents $C_{1-6}$ alkyl;
   and
   (c) one or more sugars.

2. The method according to claim 1 in which the aqueous suspension or solution further comprises at least one antigen.

3. The method according to claim 1 in which:
   the compound of formula (I) is a compound of formula (IA) or a physiologically acceptable salt or ester thereof

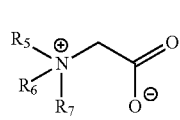

(IA)

wherein $R_5$ and $R_6$ independently represent $C_{1-4}$ alkyl and $R_7$ represents $C_{1-4}$ alkyl or —$(CH_2)_{2-5}$NHC(O)$(CH_2)_{5-15}$CH$_3$; or
   the compound of formula (I) is a compound of formula (IB) or a physiologically acceptable salt or ester thereof:

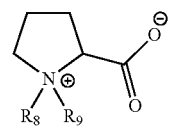

(IB)

wherein $R_8$ and $R_9$ independently represent $C_{1-4}$ alkyl.

4. The method according to claim 1 in which the compound of formula (I) is a N,N-di($C_{1-6}$ alkyl)- , N,N,N-tri($C_{1-6}$alkyl)- , or N—$C_{1-6}$ alkyl-glycine or a physiologically acceptable salt or ester thereof.

5. The method according to claim 4 in which the compound of formula (I) is N,N-dimethylglycine, N,N,N-trimethylglycine, or N-methylglycine or a physiologically acceptable salt or ester thereof.

6. The method according to claim 5 in which the compound of formula (I) is N,N-dimethylglycine or a physiologically acceptable salt or ester thereof.

7. The method according to claim 1 in which the compound of formula (I) is trimethylglycine, cocamidopropyl betaine, or proline betaine, or a physiologically acceptable salt or ester thereof.

8. The method according to claim 1 wherein the aluminium salt adjuvant is aluminium phosphate or aluminium hydroxide.

9. The method according to claim 2 wherein the at least one antigen is provided absorbed on the adjuvant.

10. The method according to claim 1 wherein the concentration of the compound of formula (I) or physiologically acceptable salt or ester thereof is at least 0.1M.

11. The method according to claim 1 wherein one sugar is used.

12. The method according to claim 1 wherein (a) the sugar is sucrose, the concentration of sucrose is from 0.01 to 0.5M or from 0.01 to 0.2M and the concentration of the compound of formula (I) or physiologically acceptable salt or ester thereof is from 0.2 to 5M, or (b) the sugar is sucrose, the concentration of sucrose is from 0.01 to 0.5M or from 0.01 to 0.2M and the concentration of the compound of formula (I) or physiologically acceptable salt or ester thereof is from 0.2 to 2M, or (c) the sugar is mannitol, the concentration of mannitol is from 0.2 to 0.8M and the concentration of the compound of formula (I) or physiologically acceptable salt or ester thereof is from 0.5 to 1 M, or (d) the sugar is sucrose and the concentration of sucrose is from 0.01 to 0.7M or 0.01. to 0.6M or 0.01 to 0.5M.

13. The method according to claim 1 wherein two or more sugars are used.

14. The method according to claim 13 wherein (a) sucrose is present with another sugar and the other sugar is raffinose, stachyose or a sugar alcohol, or (b) sucrose is present with another sugar and the other sugar is raffinose.

15. The method according to claim 1 wherein (a) the suspension or solution is freeze-dried, or (b) the suspension or solution is freeze-dried to form an amorphous solid matrix.

16. The method according to claim 15 wherein a dried amorphous solid matrix is formed and the solid matrix is provided in the form of a powder in a sealed vial, ampoule or syringe.

17. The method according to claim 15 wherein (a) the resulting cake is milled to form a powder and the powder is provided in a sealed vial, ampoule or syringe, or (b) the solid matrix forms part of tablet or capsule.

18. A vaccine composition comprising:
an aluminium-salt adjuvant as defined in claim 1;
one or more antigens;
a compound of formula (I) as defined in claim 1 or a physiologically acceptable salt or ester thereof; and
one or more sugars.

19. A vaccine composition obtainable by a method as defined in claim 2.

* * * * *